United States Patent
Simmonds

(10) Patent No.: US 11,534,417 B2
(45) Date of Patent: Dec. 27, 2022

(54) ENHANCED EXPRESSION OF RNA VECTORS

(71) Applicant: UNIVERSITY COURT OF THE UNIVERSITY OF EDINBURGH, Edinburgh Midlothian (GB)

(72) Inventor: Peter Simmonds, Edinburgh (GB)

(73) Assignee: UNIVERSITY COURT OF THE UNIVERSITY OF EDINBURGH, Edinburgh Midlothian (GB)

( * ) Notice: Subject to any disclaimer, the term of this patent is extended or adjusted under 35 U.S.C. 154(b) by 1027 days.

(21) Appl. No.: 16/122,376

(22) Filed: Sep. 5, 2018

(65) Prior Publication Data

US 2019/0060262 A1 Feb. 28, 2019

Related U.S. Application Data

(62) Division of application No. 14/779,069, filed as application No. PCT/GB2014/050917 on Mar. 24, 2014, now abandoned.

(30) Foreign Application Priority Data

Mar. 25, 2013 (GB) ..................................... 1305361

(51) Int. Cl.
*A61K 31/19* (2006.01)
*C12N 15/86* (2006.01)
*A23K 20/174* (2016.01)
*A23K 20/24* (2016.01)
*A23L 7/117* (2016.01)
*A23L 33/16* (2016.01)
*A23L 33/15* (2016.01)
*A61K 9/00* (2006.01)
*A61K 31/14* (2006.01)
*A61K 31/519* (2006.01)
*A61K 31/714* (2006.01)
*A61K 33/26* (2006.01)
*A61K 45/06* (2006.01)

(52) U.S. Cl.
CPC ............ *A61K 31/19* (2013.01); *A23K 20/174* (2016.05); *A23K 20/24* (2016.05); *A23L 7/117* (2016.08); *A23L 33/15* (2016.08); *A23L 33/16* (2016.08); *A61K 9/00* (2013.01); *A61K 31/14* (2013.01); *A61K 31/519* (2013.01); *A61K 31/714* (2013.01); *A61K 33/26* (2013.01); *A61K 45/06* (2013.01); *C12N 15/86* (2013.01); *A23V 2002/00* (2013.01); *C12N 2760/00043* (2013.01); *C12N 2760/00051* (2013.01); *C12N 2760/16143* (2013.01); *C12N 2770/00043* (2013.01); *C12N 2770/00051* (2013.01); *C12N 2770/32043* (2013.01)

(58) Field of Classification Search
None
See application file for complete search history.

(56) References Cited

U.S. PATENT DOCUMENTS

| 2011/0027317 | A1 | 2/2011 | Lewis |
| 2011/0104130 | A1 | 5/2011 | Medin |
| 2011/0123485 | A1 | 5/2011 | Desrosiers |
| 2014/0199279 | A1 | 7/2014 | Down |

OTHER PUBLICATIONS

Nougairede et al., "Random Codon Re-encoding Induces Stable Reduction of Replicative Finess of Chikungunya Virus in Primate and Mosquito Cells" 9(2) PLOS Pathogens e1003172 1-18 (Year: 2013).*
Russell et al., "Doublet Frequency Analysis of Fractionated Vertebrate Nuclear DNA" 108 Journal of Molecular Biology 1-23 (Year: 1976).*
Lohmann et al., "Replication of Subgenomic Hepatitis C Virus RNAs in a Hepatoma Cell Line" 285(5424) Science 110-113 (Year: 1999).*
Simmonds et al., "Detection of genome-scale ordered RNA structure (GORS) in genomes of positive-stranded RNA viruses: Implications for virus evolution and host persistence" 10 RNA 1337-1351 (Year: 2004).*
Krieger et al., "Enhancement of Hepatitis C Viurs RNA Replication by Cell Culture-Adaptive Mutations" 75(10) Journal of Virology 4614-4624 (Year: 2001).*
Washenberger et al., "Hepatits C Virus RNA: Dinucleotide Frequencies and Cleavage by RNase L" 130(1-2) Virus Research 85-95 (Year: 2007).*
Greenbaum et al., "Patterns of Oligonucleotide Sequences in Viral and Host Cell RNA Identify Mediators of the Host Innate Immune System" 4(6) PLoS ONE e5969 1-11 (Year: 2009).*
Coleman et al., "Virus Attenuation by Genome-Scale Changes in Codon Pair Bias" 320(5884) Science 1784-1787 (Year: 2008).*
Burge et al., Over-and under-representation of short oligonucleotides in DNA sequences 89 Proceedings of the National Academy of Sciences USA 1358-1362 (Year: 1992).*
Goodfellow et al. "Identification of a cis-Acting Replication Element within the Poliovirus Coding Region" 74(10 Journal of Virology 4590-4600 (Year: 2000).*
Duan et al., "Mammalian Mutation Pressure, Synonymous Codon Choice, and mRNA Degradation" 57 Journal of Molecular Evolution694-701 (Year: 2003).*
NM_000169.2 (*Homo sapiens* galactosidase, alpha (GLA), mRNA, NCBI Reference Sequence, priority to Apr. 9, 2011).
Burns et al. (2006) Modulation of Poliovirus Replicative Fitness in HeLa Cells by Deoptimization of Synonymous Codon Usage in the Capsid Region. Journal of Virology, 80(7):3259-3272.

(Continued)

*Primary Examiner* — Nancy J Leith
(74) *Attorney, Agent, or Firm* — Burns & Levinson LLP; Shawn P. Foley; Chris Lorenc

(57) ABSTRACT

The present invention relates to methods and compositions for enhancing expression from RNA expression vectores. The invention is based upon the observation that reducing the frequency of the dinucleotide CpG and UpA has a significant effect on expression from such vectores. Aspects of the invention include, amongst others, synthetic RNA vectores, virions, cells, methods of producing vaccines and methods of treatment or immunisation.

20 Claims, 10 Drawing Sheets

Specification includes a Sequence Listing.

(56) References Cited

OTHER PUBLICATIONS

Burns et al. (2009) Genetic Inactivation of Poliovirus Infectivity by Increasing the Frequencies of CpG and UpA Dinucleotides Within and Across Synonymous Capsid Region Codons. Journal of Virology, 83(19):9957-9969.
Palmenberg et al. (1997) Topological Organization of Picornaviral Genomes: Statistical Prediction of RNA Structural Signals Seminars in Virology,8:231-241.
Peter Simmonds, "SSE: A Nucleotide and Amino Acid Sequence Analysis Platform," BMC Research Notes, 5(1):50 (Jan. 20, 2012).
Peter Simmonds, et al., "Structural Constraints on RNA Virus Evolution," Journal of Virology, vol. 73, No. 7, pp. 5787-5794 (Jul. 1999).
Atkinson, Nicky J., et al., "The Influence of CpG and UpA Dinucleotide Frequencies on RNA Virus Replication and Characterization of the Innate Cellular Pathways Underlying Virus Attenuation and Enhanced Replication," Nucleic Acids Research, vol. 42, No. 7, pp. 4527-4545 (Jan. 26, 2014), XP002725549.
Lauring, Adams S., et al., "Codon Usage Determines the Mutational Robustness, Evolutionary Capacity, and Virulence of an RNA Virus," Cell Host & Microbe, vol. 12, No. 5, pp. 623-632 (Nov. 2012), XP002725550.
Karlin S., et al., "Why is CpG Suppressed in the Genomes of Virtually All Small Eukaryotic Viruses but Not in Those of Large Eukaryotic Viruses?", Journal of Virology, The American Society for Microbiology, US, vol. 68, No. 5, pp. 2889-2897 (May 1, 1994), XP000986332.

Simmonds, Peter, et al., Modelling Mutational and Selection Pressures on Dinucleotides in Eukaryotic Phyla-Selection Against CpG and UpA in Cytoplasmically Expressed RNA and in RNA vir11, BMC Genomics, Biomed Central Ltd., London, UK, vol. 14, No. 1 (Sep. 10, 2013), XP021167504, ISSN: 1471-2164.
Rima, Bertus K., et al., "Dinucleotide and Stop Codon Frequencies in Single-Stranded RNA Viruses," Journal of General Virology, vol. 78, No. 11, pp. 2859-2870 (Nov. 1997), XP002725551, ISSN: 0022-1317.
Bauer S., et al., "Human TLR9 Confers Responsiveness to Bacterial DNA via Species-Specific CpG Motif Recognition," Proceedings of the National Academy of Sciences, National Academy of Sciences, US, vol. 98, No. 16 (Jul. 31, 2001), XP002221247, ISSN: 0027-8424.
Lund, Jennifer M., et al., "Recognition of Single-Stranded RNA Viruses by Toll-Like Receptor 7," Proceedings of the National Academy of Sciences of the United States of America, vol. 101, No. 15, pp. 5598-5603 (Apr. 13, 2001), XP002725552, ISSN: 0027-8424.
EPO, International Search Report (dated Jun. 12, 2014).
EPO, Written Opinion of the International Searching Authority (dated Jun. 12, 2014).
DQ205100.1, "Synthetic Construct Clone S2R23, NCBI Reference Sequence," priority to Mar. 13, 2009, 3 pages, (2006).
Watts et al., (2009), "Architecture and Secondary Structure of an Entire HIV-1 RNA Genome," Nature, 460:711-716, 2009.

* cited by examiner

Plaque photos

Plaque measurements

SEQUENCE LISTING

```
<160> NUMBER OF SEQ ID NOS: 34

<210> SEQ ID NO 1
<211> LENGTH: 1245
<212> TYPE: RNA
<213> ORGANISM: Echovirus 7

<400> SEQUENCE: 1
gucgacuccg uggugcccgu caacaauauc aaagucaacc ugcaaagcau ggaugcguau      60
cauauugagg ucaauaccgg gaaccaccag ggggaaaaga uuuuugcguu ccaaaugcag     120 ccggggeuuag agucuguuuu caagagaacc cuuauggggg agauucuuaa uuauuaugca    180
cacuggucag ggagcauuaa gcugacauuc acauuuugug gaucggcgau ggcaacugga    240
aaacucuugu uagcguauuc accaccaggu gcugaugugc ccgcgaccag gaaacaggcg    300
```

| | |
|---|---:|
| auguuaggca cacacaugau uugggauauc gggcuucagu cgagcugugu uuugugcauc | 360 |
| ccauggauaa gucagacaca cuaccgguua gugcaacaag augaauacac gagugcaggc | 420 |
| aaugugacgu guugguacca acaggaauau gugugccccc cuggcacucc aaauaagugu | 480 |
| guagugcuuu guuuugcauc agcuuguaau gauuucucag uucgaaugcu uagggacacc | 540 |
| ccuuucaucg gacaaacagc acugcugcaa ggcgacaccg aaacggcuau ugacaaugca | 600 |
| aucgccaggg uagcagauac gguggcgagc gguccuagua auucgaccag uaucccagca | 660 |
| cucacagcag uugagacagg ucacacguca caagucgagc ccagcgauac aaugcagacu | 720 |
| agacauguca aaacuacca cucgcguucu gagucaaccg uggaaaacuu ucuaagucgc | 780 |
| uccgcuugug uguacaucga agaguacuac accaaggacc aagacaaugu aauaagguac | 840 |
| augucgugga caauaaaugc cagaagaaug gugcaauuga ggagaaaguu ugagcuguuu | 900 |
| acauacauga gauuugauau ggaaaucacg uuuguaauca caaguagaca acuaccuggg | 960 |
| acuagcauag cacaagauau gccgccacuc acccaccaga ucauguacau accaccaggu | 1020 |
| ggcccgguac caaacagcgu aacagauuuu gcguggcaga caucaacaaa ccccagcauu | 1080 |
| uucuggacag aaggaaacgc gccaccucgc augucuauuc cauucaucag uauuggcaau | 1140 |
| gcauauagca acuucuauga cggguggucu cacuuucccc aaaacggugu guacggauac | 1200 |
| aacgcccuga caacauggg caagcuguac gcacgucaug uuaac | 1245 |

<210> SEQ ID NO 2
<211> LENGTH: 1029
<212> TYPE: RNA
<213> ORGANISM: Echovirus 7

<400> SEQUENCE: 2

| | |
|---|---:|
| gaauucgccg uugcuaugau gaagagaaac ucaaguacag ugaagacuga guauggugag | 60 |
| uuuacuaugc ugggcaucua ugacaagugg gccguuuugc cacgccaugc uaaaccugga | 120 |
| ccaaccaucc ugaugaauga ccaagagguc ggcguguuga cgccaaggga acuaguggac | 180 |
| aaggauggca cuaaccugga gcugacacua ucaaguuaa accggaauga gaaguucaga | 240 |
| gacaucagag gcuucuuggc uaaggaggaa gugggaaguca acgaggcugu gcuggcaaua | 300 |
| aacacuagca aguuccuaa caugugacauu ccaguagggc agguuacaga uuacggcuuc | 360 |
| cuaaaccugg gugguacacc caccaaaaga augcuuaugu auaacuuccc cacaagagca | 420 |
| ggccagugug gcgggguacu caugucccacu ggcaaaguuu ugggaaucca guuggugga | 480 |
| aauggccauc aaggcuucuc agcagcacuu ucaaacacu acuuuaauga ugaacaagga | 540 |
| gagauugagu ucauugagag uucaaaggaa gcagggguucc caaucauuaa cgcacccagu | 600 |
| aaaaccaagc uggagccaag ugucuuccac caaguauuug aaggcaacaa agagccagca | 660 |
| guccucagga cagugacccc acgucucaaa gcuaauuucg aggaggccau cuuuuccaaa | 720 |
| uacauuggga augucaacac acacauagau gaauacaugu uggaggcugu ugaccauuau | 780 |
| gccggacaau uggccacccu agauaucagc acugaaccaa ugaaguugga ggaugcugug | 840 |
| uacgguacug aaggccuuga agcucuugac uuaacaacaa gugcaggcua ccccuaugug | 900 |
| gcacugggua ucaagaagag agacauccuc ucgaagaaga ccaaggaccu gaccaagcug | 960 |
| aaagagugca uggauaagua uggccugaau cuaccaaugg ugacauacgu gaaagaugaa | 1020 |
| cucagaucu | 1029 |

<210> SEQ ID NO 3
<211> LENGTH: 1245

```
<212> TYPE: RNA
<213> ORGANISM: Artificial Sequence
<220> FEATURE:
<223> OTHER INFORMATION: CpG-low Region 1

<400> SEQUENCE: 3
gucgacucag uggugccagu caacaauauc aaagucaacc ugcaaagcau ggaugcuuau      60
cauauugagg ucaauacagg gaaccaccag ggggaaaaga uuuugcuuu ccaaaugcag     120
ccuggguuag agucuguuuu caagagaacc cuuauggggg agauucuuaa uuauuaugca    180
cacuggucag ggagcauuaa gcugacauuc acauuuugug gaucugccau ggcaacugga    240
aaacucuugu uagcuuauuc accaccaggu gcugaugugc cugcaaccag gaaacaggcu    300
auguuaggca cacacaugau uugggauaua gggcuucagu ccagcugugu uugugcauc     360
ccauggauaa gucagacaca cuacagguua ugcaacaag augaauacac aagugcaggc     420
aaugugacau guuggaucca aacaggaaua gugugccccc cuggcacucc aaauaagugu    480
guagugcuuu guuugcauc agcuuguaau gauuucucag uuaggaugcu uagggacacc     540
ccuuucauag gacaaacagc acugcugcaa ggagacacag aaacagcuau ugacaaugca    600
auugccaggg uagcagauac uguggcaagu gguccuagua auucaaccag uaucccagca    660
cucacagcag uugagacagg ucacaccuca caagggagc ccagugauac aaugcagacu     720
agacauguca aaaacuacca cucuaggucu gagucaacug uggaaaacuu ucuaaguagg    780
ucagcuugug uguacauaga agaguacuac accaaggacc aagacaaugu uaauaagguac   840
auguccugga caauaaaugc cagaagaaug gugcaauuga ggagaaaguu ugagcuguuu    900
acauacauga gauuugauau ggaaaucacc uuuguaauca caguagaca acuaccuggg     960
acuagcauag cacaagauau gccaccacuc acccaccaga ucauguacau accaccaggu   1020
ggcccaguac caaacagugu aacagauuuu gccuggcaga caucaacaaa ccccagcauu   1080
uucuggacag aaggaaaugc cccaccuagg augucuauuc cauucaucag uauuggcaau   1140
gcauauagca acuucuauga uggguggca cacuuuccc aaaauggugu guauggauac     1200
aaugcccuga caacaugggg caagcuguau gcaagacaug uuaac                    1245

<210> SEQ ID NO 4
<211> LENGTH: 1029
<212> TYPE: RNA
<213> ORGANISM: Artificial Sequence
<220> FEATURE:
<223> OTHER INFORMATION: CpG-low Region 2

<400> SEQUENCE: 4
gaauucgcug uugcuaugau gaagagaaac ucaaguacag ugaagacuga guaugaugag    60
uuuacuaugc uggcaucua ugacaagugg gcaguuuugc caaggcaugc uaaaccugga    120
ccaaccaucc ugaugaauga ccaagaggu ggggugguuag augccaagga acuaguggac    180
aaggauggca cuaaccugga gcugacacua cucaaguuaa acagaaauga gaaguucaga    240
gacaucagag gcuucuuggc uaaggaggaa gugaaaguca augaggcugu gcuggcaaua    300
aacacuagca aguuuccuaa caugaucauu ccaguagggc agguuacaga uuauggcuuc    360
cuaaaccugg gugguacacc caccaaaaga augcuuaugu auaacuuccc cacaagagca    420
ggccaguug gaggguguacu caugaccacu ggcaaaguuu ugggaaucca uguuggugga    480
aauggccauc aaggcuucuc agcagcacuu cucaaacacu acuuuaauga ugaacaagga    540
gagauugagu ucauugagag uucaaaggaa gcaggguucc caaucauuaa ugcacccagu    600
```

| | |
|---|---|
| aaaaccaagc uggagccaag ugucuuccac caaguauuug aaggcaacaa agagccagca | 660 |
| guccucagga acagugaccc aaggcucaaa gcuaauuuug aggaggccau cuuuuccaaa | 720 |
| uacauuggga augucaacac acacauagau gaauacaugu uggaggcugu ugaccauuau | 780 |
| gcaggacaau uggccacccu agauaucagc acugaaccaa ugaaguugga ggaugcugug | 840 |
| uaugguacug aaggccuuga agcucuugac uuaacaacaa gugcaggcua ccccuaugug | 900 |
| gcacugggua ucaagaagag agacauccuc ucaaagaaga ccaaggaccu gaccaagcug | 960 |
| aaagagugca uggauaagua uggccugaau cuaccaaugg ugacauaugu gaaagaugaa | 1020 |
| cucagaucu | 1029 |

<210> SEQ ID NO 5
<211> LENGTH: 1245
<212> TYPE: RNA
<213> ORGANISM: Artificial Sequence
<220> FEATURE:
<223> OTHER INFORMATION: UpA-low Region 1

<400> SEQUENCE: 5

| | |
|---|---|
| gucgacuccg uggugcccgu caacaacauc aaagucaacc ugcaaagcau ggaugcguau | 60 |
| cacauugagg ucaacaccgg gaaccaccag ggggaaaaga uuuuugcguu ccaaaugcag | 120 |
| ccgggguugg agucuguuuu caagagaacc cucauggggg agauucucaa uuauuaugca | 180 |
| cacuggucag ggagcaucaa gcugacauuc acauuuugug gaucggcgau ggcaacugga | 240 |
| aaacucuugu uggcguauuc accaccaggu gcugaugugc ccgcgaccag gaaacaggcg | 300 |
| auguggggca cacacaugau uugggacauc gggcuucagu cgagcugugu uugugcauc | 360 |
| ccauggauca gucagacaca cuaccgguug gugcaacaag augaauacac gagugcaggc | 420 |
| aaugugacgu guugguacca aacaggaauu guggugcccc cuggcacucc aaacaagugu | 480 |
| gucgugcuuu guuuugcauc agcuugcaau gauuucucag uucgaaugcu gagggacacc | 540 |
| ccuuucaucg gacaaacagc acugcugcaa ggcgacaccg aaacggcgau ugacaaugca | 600 |
| aucgccaggg uugcagacac gguggcgagc gguccgagca auucgaccag caucccagca | 660 |
| cucacagcag uugagacagg ucacgucaca caagucgagc ccagcgacac aaugcagacc | 720 |
| agacauguca aaaacuacca cucgcguucu gagucaaccg uggaaaacuu ucucagucgc | 780 |
| uccgcuugug uguacaucga agauacuac accaaggacc aagacaaugu caacagguac | 840 |
| augucgugga caaucaaugc cagaagaaug gugcaauuga ggagaaaguu ugagcuguuc | 900 |
| acauacauga gauuugacau ggaaaucacg uuugucauca aagcagaca acuuccuggg | 960 |
| acgagcaucg cacaagacau gccgccacuc acccaccaga ucauguacau cccaccaggu | 1020 |
| ggcccggucc caaacagcgu cacagauuuu gcguggcaga caucaacaaa ccccagcauu | 1080 |
| uucuggacag aaggaaacgc gccaccucgc auguccauuc cauucaucag cauuggcaau | 1140 |
| gcauacagca acuucuauga cgggugguca cacuuuuccc aaaacggugu guacggauac | 1200 |
| aacgcccuga acaacauggg caagcuguac gcacgucaug uuaac | 1245 |

<210> SEQ ID NO 6
<211> LENGTH: 1029
<212> TYPE: RNA
<213> ORGANISM: Artificial Sequence
<220> FEATURE:
<223> OTHER INFORMATION: UpA-low Region 2

<400> SEQUENCE: 6

| | |
|---|---|
| gaauucgccg uugccaugau gaagagaaac ucaagcacag ugaagacuga guauggugag | 60 |

| | | |
|---|---|---|
| uucacgaugc ugggcaucua ugacaagugg gccguuuugc cacgccaugc caaaccugga | 120 | |
| ccaaccauuc ugaugaauga ccaagagguc ggcguguugg acgccaagga acuggggac | 180 | |
| aaggauggca caaaccugga gcugacacuc ucaaguuga accggaauga gaaguucaga | 240 | |
| gacaucagag gcuucuuggc gaaggaggaa guggaaguca acgaggcugu gcuggcaauc | 300 | |
| aacaccagca aguuuccaaa caugua cauu ccaguuggggc aggucacaga uuacggcuuc | 360 | |
| cugaaccugg gugggacacc caccaaaaga augcucaugu acaacuuccc cacaagagca | 420 | |
| ggccagugug gcgggugcu caugccacu ggcaaaguuu ugggaaucca guuggugga | 480 | |
| aauggccauc aaggcuucuc agcagcacuu ucaaacacu acuucaauga ugaacaagga | 540 | |
| gagauugagu ucauugagag uucaaggaa gcagggguucc caaucaucaa cgcacccagc | 600 | |
| aaaaccaagc uggagccaag ugucuuccac caaguguuu aaggcaacaa agagccagca | 660 | |
| guccucagga acagugaccc acgucucaaa gccaauucg aggaggccau cuuuuccaaa | 720 | |
| uacauuggga augucaacac acacaucgau gaauacaugu uggaggcugu ugaccauuau | 780 | |
| gccggacaau uggccacccu ugacaucagc acugaaccaa ugaaguugga ggaugcugug | 840 | |
| uacggcacug aaggccuuga agcucuugac uugacaacaa gugcaggcua ccccuaugu c| 900 | |
| gcacugggga ucaagaagag agacauccuc ucgaagaaga ccaaggaccu gaccaagcug | 960 | |
| aaagagugca uggacaagua uggccugaau cuuccaaugg ugacauacgu gaaagaugaa | 1020 | |
| cucagaucu | 1029 | |

<210> SEQ ID NO 7
<211> LENGTH: 1245
<212> TYPE: RNA
<213> ORGANISM: Artificial Sequence
<220> FEATURE:
<223> OTHER INFORMATION: CpG and UpA-low Region 1

<400> SEQUENCE: 7

| | | |
|---|---|---|
| gucgacucag uggugccagu caacaacauc aaagucaacc ugcaaagcau ggaugcuuau | 60 | |
| cacauugagg ucaacacagg gaaccaccag ggggaaaaga uuuuugcuuu ccaaaugcag | 120 | |
| ccuggguugg agucuguuuu caagagaacc cugauggggg agauucugaa uuauuaugca | 180 | |
| cacuggucag ggagcaucaa gcugacauuc acauuuugug gaucugccau ggcaacugga | 240 | |
| aaacucuugu uggcuuauuc accaccaggu gcugaugugc cugcaaccag gaaacaggcc | 300 | |
| auguugggca cacacaugau uugggacauu gggcuucagu ccagcugugu uuugugcauc | 360 | |
| ccauggauca gucagacaca cuacagguug gugcaacaag augaauacac aagugcaggc | 420 | |
| aaugugacau guuggua cca aacaggaauu guggugccccc cuggcacucc aaacaagugu | 480 | |
| guugugcuuu guuugcauc agcuugcauu gauuucucag ucaggaugcu cagggacacc | 540 | |
| ccuuucauug acaaacagc acugcugcaa ggagacacag aaacagccau ugacaaugca | 600 | |
| auugccaggu uugcagacac uguggcaagu ggu ccaagca auucaaccag caucccagca | 660 | |
| cucacagcag uugagacagg ucacaccuca caaguggagc ccagugacac aaugcagaca | 720 | |
| agacauguca aaacuacca cuccaggucu gagucaacug ggaaaacuu ucucagcagg | 780 | |
| ucagcuugug uguacauuga agaguacuac accaaggacc aagacaaugu caacagguac | 840 | |
| auguccugga caaucaaugc cagaagaaug gugcaauuga ggagaaaguu ugagcuguuc | 900 | |
| acauacauga gauuugacau ggaaaucacc uuugugauca aagcagaca acucccuggg | 960 | |
| acaagcauug cacaagacau gccaccacuc acccaccaga ucauguacau uccaccaggu | 1020 | |

```
ggcccagugc caaacagugu cacagauuuu gccuggcaga caucaacaaa ccccagcauu      1080
uucuggacag aaggaaaugc cccaccaagg auguccauuc cauucaucag cauuggcauu      1140
gcauacagca acuucuauga ugggugguca cacuuuuccc aaaaugugug guauggauac      1200
aaugcccuga caacaugggc aagcuguau gcaagacaug uuaac                       1245

<210> SEQ ID NO 8
<211> LENGTH: 1029
<212> TYPE: RNA
<213> ORGANISM: Artificial Sequence
<220> FEATURE:
<223> OTHER INFORMATION: CpG and UpA-low Region 2

<400> SEQUENCE: 8
gaauucgcug uugccaugau gaagagaaac ucaagcacag ugaagacuga guauggugag        60
uucaccaugc ugggcaucua ugacaagugg gcaguuuugc caaggcaugc caaaccugga      120
ccaaccaucc ugaugaauga ccaagagguu ggggguguugg augccaagga acuggaggac      180
aaggauggca ccaaccugga gcugacacuu cucaaguuga acagaaauga gaagacagua      240
gacaucagag gcuucuuggc caaggaggaa guggaaguca augaggcugu gcuggcaauc      300
aacaccagca aguuucccaa cauguacauu ccagugggc aggugacaga uuauggcuuc       360
cugaaccugg guggaacacc caccaaaaga augcucaugu acaacuuccc cacaagagca      420
ggccagugug gagggguucu caugccacu ggcaaaguuu ugggaaucca guuggugga       480 aauggccauc aaggcuucuc agcagcacuu cucaaacacu acuucaauga ugaacaagga      540
gagauugagu cauugagag uucaaaggaa gcagggguucc caaucaucaa ugcacccagc      600
aaaaccaagc uggagccaag ugucuuccac caaguguuug aaggcaacaa agagccagca      660
guccucagga acaguggaccc aaggcucaaa gccaauuuug aggaggccau cuuuuccaaa      720
uacauuggga augucaacac acacauugau gaauacaugu ggaggcugu ugaccauuau      780 gcaggacaau uggccacccu ggacaucagc acugaaccaa ugaaguugga ggaugcugug      840
uauggcacug aaggccuuga agcucuugac uugacaacaa gugcaggcua ccccuaugug      900
gcacuggggc ucaagaagag agacauccuc ucaaagaaga ccaaggaccu gaccaagcug      960
aaagagugca uggacaagua uggccugaau cucccaaugg ugacauaugu gaaagaugaa      1020
cucagaucu                                                             1029

<210> SEQ ID NO 9
<211> LENGTH: 22
<212> TYPE: DNA
<213> ORGANISM: Artificial Sequence
<220> FEATURE:
<223> OTHER INFORMATION: E7 qRT-PCR sense primer

<400> SEQUENCE: 9
tccggcccct gaatgcggct aa                                                22

<210> SEQ ID NO 10
<211> LENGTH: 22
<212> TYPE: DNA
<213> ORGANISM: Artificial Sequence
<220> FEATURE:
<223> OTHER INFORMATION: E7 qRT-PCR antisense primer

<400> SEQUENCE: 10
cacccaaagt agtcggttcc gc                                                22
```

<210> SEQ ID NO 11
<211> LENGTH: 27
<212> TYPE: DNA
<213> ORGANISM: Artificial Sequence
<220> FEATURE:
<223> OTHER INFORMATION: outer, sense sequencing primer

<400> SEQUENCE: 11
cccaatttga tgtaacacca cacatgg                                27

<210> SEQ ID NO 12
<211> LENGTH: 25
<212> TYPE: DNA
<213> ORGANISM: Artificial Sequence
<220> FEATURE:
<223> OTHER INFORMATION: inner, sense sequencing primer

<400> SEQUENCE: 12
gatattccag gcgaagtaca caacc                                  25

<210> SEQ ID NO 13
<211> LENGTH: 25
<212> TYPE: DNA
<213> ORGANISM: Artificial Sequence
<220> FEATURE:
<223> OTHER INFORMATION: EV7 WT, outer, antisense sequencing primer

<400> SEQUENCE: 13
caaagcacta cacacttatt tggag                                  25

<210> SEQ ID NO 14
<211> LENGTH: 22
<212> TYPE: DNA
<213> ORGANISM: Artificial Sequence
<220> FEATURE:
<223> OTHER INFORMATION: R1/R2 CpG-high, outer, antisense sequencing
      primer

<400> SEQUENCE: 14
attcgaacgg agaaatcgtt ac                                     22

<210> SEQ ID NO 15
<211> LENGTH: 25
<212> TYPE: DNA
<213> ORGANISM: Artificial Sequence
<220> FEATURE:
<223> OTHER INFORMATION: R1/R2 UpA-high, outer, antisense sequencing
      primer

<400> SEQUENCE: 15
tcccttagca tacgtactga gaaat                                  25

<210> SEQ ID NO 16
<211> LENGTH: 21
<212> TYPE: DNA
<213> ORGANISM: Artificial Sequence
<220> FEATURE:
<223> OTHER INFORMATION: EV7 WT, inner, antisense sequencing primer

<400> SEQUENCE: 16
gcaccactat tcctgtttgg t                                      21

<210> SEQ ID NO 17
<211> LENGTH: 22
<212> TYPE: DNA
<213> ORGANISM: Artificial Sequence
<220> FEATURE:

<223> OTHER INFORMATION: R1/R2 CpG-high, inner, antisense sequencing primer

<400> SEQUENCE: 17
aacaaagcac gacgcactta tt    22

<210> SEQ ID NO 18
<211> LENGTH: 25
<212> TYPE: DNA
<213> ORGANISM: Artificial Sequence
<220> FEATURE:
<223> OTHER INFORMATION: R1/R2 UpA-high, inner, antisense sequencing primer

<400> SEQUENCE: 18
cattacaagc tgatgcaaaa catag    25

<210> SEQ ID NO 19
<211> LENGTH: 20
<212> TYPE: DNA
<213> ORGANISM: Artificial Sequence
<220> FEATURE:
<223> OTHER INFORMATION: outer, sense sequencing primer

<400> SEQUENCE: 19
tgagcccgta catcaaatca    20

<210> SEQ ID NO 20
<211> LENGTH: 20
<212> TYPE: DNA
<213> ORGANISM: Artificial Sequence
<220> FEATURE:
<223> OTHER INFORMATION: inner, sense sequencing primer

<400> SEQUENCE: 20
ttttaacccc acgaacctga    20

<210> SEQ ID NO 21
<211> LENGTH: 20
<212> TYPE: DNA
<213> ORGANISM: Artificial Sequence
<220> FEATURE:
<223> OTHER INFORMATION: outer, antisense sequencing primer

<400> SEQUENCE: 21
ttgccgagtt gttcgacata    20

<210> SEQ ID NO 22
<211> LENGTH: 20
<212> TYPE: DNA
<213> ORGANISM: Artificial Sequence
<220> FEATURE:
<223> OTHER INFORMATION: inner, antisense sequencing primer

<400> SEQUENCE: 22
caagtcacgg atgtctgcaa    20

<210> SEQ ID NO 23
<211> LENGTH: 27
<212> TYPE: DNA
<213> ORGANISM: Artificial Sequence
<220> FEATURE:
<223> OTHER INFORMATION: region 1 sense (outer) PCR primer

<400> SEQUENCE: 23
cccaatttga tgtaacacca cacatgg    27

<210> SEQ ID NO 24
<211> LENGTH: 25
<212> TYPE: DNA
<213> ORGANISM: Artificial Sequence
<220> FEATURE:
<223> OTHER INFORMATION: region 1 sense (inner) PCR primer

<400> SEQUENCE: 24
gatattccag gcgaagtaca caacc                                    25

<210> SEQ ID NO 25
<211> LENGTH: 22
<212> TYPE: DNA
<213> ORGANISM: Artificial Sequence
<220> FEATURE:
<223> OTHER INFORMATION: region 1 antisense (outer) PCR primer

<400> SEQUENCE: 25
cccatactcg gatgtgcttg gg                                       22

<210> SEQ ID NO 26
<211> LENGTH: 24
<212> TYPE: DNA
<213> ORGANISM: Artificial Sequence
<220> FEATURE:
<223> OTHER INFORMATION: region 1 antisense (inner) PCR primer

<400> SEQUENCE: 26
cactcggatt gtgcttgaca tctg                                     24

<210> SEQ ID NO 27
<211> LENGTH: 23
<212> TYPE: DNA
<213> ORGANISM: Artificial Sequence
<220> FEATURE:
<223> OTHER INFORMATION: region 2 sense (outer) PCR primer

<400> SEQUENCE: 27
caaggagcat acacaggaat acc                                      23

<210> SEQ ID NO 28
<211> LENGTH: 22
<212> TYPE: DNA
<213> ORGANISM: Artificial Sequence
<220> FEATURE:
<223> OTHER INFORMATION: region 2 sense (inner) PCR primer

<400> SEQUENCE: 28
ggtacctact cttaggcaag ca                                       22

<210> SEQ ID NO 29
<211> LENGTH: 23
<212> TYPE: DNA
<213> ORGANISM: Artificial Sequence
<220> FEATURE:
<223> OTHER INFORMATION: region 2 antisense (outer) PCR primer

<400> SEQUENCE: 29
gaatgtctgc ctcatcgcca act                                      23

<210> SEQ ID NO 30
<211> LENGTH: 23
<212> TYPE: DNA
<213> ORGANISM: Artificial Sequence
<220> FEATURE:

```
<223> OTHER INFORMATION: region 2 antisense (inner) PCR primer

<400> SEQUENCE: 30
aagctggacg cttcaatgag cct                                              23

<210> SEQ ID NO 31
<211> LENGTH: 24
<212> TYPE: DNA
<213> ORGANISM: Artificial Sequence
<220> FEATURE:
<223> OTHER INFORMATION: GAPDH qRT-PCR sense primer

<400> SEQUENCE: 31
gaaatcccat caccatcttc cagg                                             24

<210> SEQ ID NO 32
<211> LENGTH: 20
<212> TYPE: DNA
<213> ORGANISM: Artificial Sequence
<220> FEATURE:
<223> OTHER INFORMATION: GAPDH qRT-PCR antisense primer

<400> SEQUENCE: 32
gagccccagc cttctccatg                                                  20

<210> SEQ ID NO 33
<211> LENGTH: 23
<212> TYPE: DNA
<213> ORGANISM: Artificial Sequence
<220> FEATURE:
<223> OTHER INFORMATION: IFN-beta qRT-PCR sense primer

<400> SEQUENCE: 33
gaccaacaag tgtctcctcc aaa                                              23

<210> SEQ ID NO 34
<211> LENGTH: 22
<212> TYPE: DNA
<213> ORGANISM: Artificial Sequence
<220> FEATURE:
<223> OTHER INFORMATION: IFN-beta qRT-PCR antisense primer

<400> SEQUENCE: 34
gaactgctgc agctgcttaa tc                                               22
```

ENHANCED EXPRESSION OF RNA VECTORS

CROSS-REFERENCE TO RELATED APPLICATIONS

This application is a divisional of U.S. application Ser. No. 14/779,069, filed on Sep. 22, 2015, now U.S. Patent Application No. US 2016/0053281, pursuant to 35 U.S.C. 371 of International Application No. PCT/GB2014/050917, filed on Mar. 24, 2014, published in English as WO 2014/155076 and entitled "Enhanced Expression of RNA Vectors". This application further claims the benefit of foreign priority to GB 1305361.6, entitled "Enhanced Expression" and which was filed on Mar. 25, 2013, through PCT/GB2014/050917 filed on Mar. 24, 2014. The entire contents of the aforementioned patent applications are incorporated herein by this reference.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Mar. 13, 2022 and is 18758 bytes in size, is named HGF-800DIV_ST25.txt.

BACKGROUND OF THE INVENTION

The present invention relates to methods for enhancing the expression of proteins by modifying the nucleotide composition of the encoding nucleic acid. In particular it relates to methods for enhancing the expression of RNA expression vectors, by reducing the frequency of CpG and/or UpA dinucleotides. The invention also relates to nucleic acids modified in such a way, and to systems in which such nucleic acids are used.

The base composition of DNA of mammals and other eukaryotes show evidence for complex selection pressures and mutational mechanisms. In vertebrates, regions of extensive under-representation of CpG dinucleotides (i.e. C followed by G) are found throughout the genome (Russell et al. 1976, J. Mol. Biol. 108: 123). This is thought to originate largely as a result of DNA methylation that has a mutagenic effect on the cytosine residue.

For example, in the human genome, which has a mean 42% G+C content, a pair of nucleotides consisting of cytosine followed by guanine would be expected to occur 0.21*0.21-0.041 the time. The actual frequency of CpG dinucleotides in human genomes is 1%-less than one-quarter of the expected frequency. It is proposed that the CpG deficiency is due to an increased vulnerability of methylcytosines to spontaneously deaminate to thymine in genomes with CpG cytosine methylation.

In a recent large scale bioinformatic analysis of various eukaryotic groups that show differing degrees of genomic DNA methylation, evidence was found for further mutational mechanisms operating on genomic DNA and evidence for strong selection against UpA and CpG dinucleotides among the subset of genomic DNA sequences that are transcribed as RNA and transported to the cytoplasm (Simmonds et al. 2013, BMC genomics, 14, 610).

A similar selection process was identified in RNA viruses infecting mammals and plants that potentially accounts for their previously described, but unexplained, under-representations of these dinucleotides (Rima and McFerran. 1997, J. Gen. Virol. 78:2859-2870). The nature of the selection against CpG and UpA dinucleotides is poorly understood and has not been investigated functionally to date.

Further evidence that the presence of CpG dinucleotides in viral sequences either activate or are targets of cell defence mechanisms is provided by the observation that polioviruses with artificially elevated CpG frequencies in their genomic RNA were markedly attenuated and replicated to titers several orders of magnitude lower than wild type virus in in vitro cell culture (1-3). This effect was independent of changes in translation efficiency through alteration of codon usage and codon pair bias.

The attenuation of poliovirus with artificially elevated CpG frequencies in their genomic RNA was additionally unrelated to differences in Toll-like receptor 9 (TLR9) signalling as the poliovirus genome is comprised of RNA which is not a substrate for TLR9. This contrasts with DNA based expression systems in which the CpG content is reduced or eliminated to enhance expression through avoidance of TLR9-induced activation of transfected cells. For example, the pCpGfree DNA plasmid vectors from Invivogen (San Diego, Calif.) are CpG free and Invivogen also provide a service in which they will create a CpG-free DNA version of a gene of interest and insert it into a pCpGfree DNA plasmid. The rationale behind this technology is that bacterial DNA is rich in unmethylated CpG dinucleotides, in contrast to mammalian DNA which contains a low frequency of CpG dinucleotides that are mostly methylated (Bauer et al. 2001, PNAS USA, 98(16):9237-42). Unmethylated CpGs in specific sequence contexts activate the vertebrate immune system via Toll-like receptor (TLR) 9. TLR9 recognizes CpG in DNA and initiates a signalling cascade leading to the production of pro-inflammatory cytokines such as IL-6 and IL-12. Plasmids used for in vivo experiments are produced in $E.$ $coli$ and therefore their CpGs are unmethylated and induce immune responses through this host defence mechanism, which represents a limitation for the clinical development of DNA vaccines and gene therapy vectors. Thus, this technology is limited to DNA-based expression systems. Furthermore, given that the TLR9 system acts only on DNA, there is no basis to believe that the rationale could extend to RNA-based expression systems There remains a need for improved systems for the expression of proteins encoded on RNA polynucleotides. In particular there is a need to improve expression of RNA expression vectors, such as RNA viral vectors, in suitable expression systems.

SUMMARY OF THE INVENTION

According to the present invention there is provided a synthetic RNA expression vector comprising a sequence encoding an expression product, the nucleic acid comprising at least one region in which the nucleotide composition has been modified such that the frequency of CpG and/or UpA dinucleotides is reduced relative to normal frequency.

The term 'synthetic RNA expression vector' refers to a nucleic acid construct formed of RNA, the construct comprising a sequence encoding an expression product and at least one regulatory sequence (e.g. a promoter) to drive expression of the expression product. The synthetic RNA expression vector can be capable of replication in a host cell or it can be replication deficient. Thus the synthetic RNA expression vector can comprise virion control elements and coding regions to allow replication in a host cell.

Suitably the synthetic RNA expression vector is a recombinant RNA viral vector, e.g. a recombinant virus genome.

Preferably the frequency of both CpG and UpA dinucleotides is reduced relative to normal frequency.

Suitably the at least one region is at least 30 nucleotides in length, more preferably at least 100 nucleotides in length, yet more preferably at least 200 nucleotides in length and suitably at least 500 nucleotides in length. In some embodiments the at least one region can be over 1000 nucleotides in length. A given synthetic RNA expression vector according to the present invention can comprise one or more than one (e.g. 2, 3, 4, 5, 6, 7, 8, 9, or 10) regions in which the CpG and/or UpA frequency region is reduced. One could view each base change to a wild type sequence as an individual 'region', and in some cases the present invention envisages such minor changes, e.g. in highly constrained synthetic RNA expression vectors. However, typically several changes are made within a longer region in order to bring about a more significant change in the frequency of CpG and/or UpA dinucleotides in a given synthetic RNA expression vector. For example, typically much or all of one or more ORFs will be modified to reduce the frequency of CpG and/or UpA dinucleotides. Many synthetic RNA expression vectors will comprise two or more ORFs, and in that case it is envisaged that regions correlating to some or all of those ORFs will be modified.

The present inventors have made the unexpected discovery that reducing the occurrence of CpG or UpA levels below those found in wild type sequences enhances their expression in RNA viral vectors. It is typically thought that sequences of such RNA viruses in their natural contexts are optimised for expression, and hence replication, in their relevant environment. Sequences in nature have evolved such that the occurrence of CpG or UpA dinucleotides is reduced relative to the statistically expected number for reasons that are not entirely clear, as discussed elsewhere in this application and the various cited documents referred to herein. It is known that increasing the occurrence of CpG or UpA dinucleotides in RNA can lead to a reduction in expression levels. However, it has not been proposed or discussed that reducing the occurrence of CpG or UpA in an RNA expression vector below those found in the wild type sequence leads to an increase in expression levels.

This finding is surprising because there is an assumption that wild type viral sequences are highly optimised for expression in their respective host. Thus one would not expect that creating a sequence which deviates significantly from the natural sequence, e.g. by reducing the occurrence of CpG and UpA dinucleotides to an artificially low level, would result in an increase in expression. It is well known that viruses are relatively free to evolve rapidly and that they are under strong evolutionary pressure in order to maximise their relationship with their host and avoid host defences. This results in viral expression systems becoming rapidly highly optimised for their host. In particular, the open reading frames (ORFs) of viral genomes encoding viral components are expected to have evolved to an optimum composition to maximise their relationship with their host. Indeed, it can be observed that the frequency of CpG and UpA dinucleotides in the ORFs of viral genomes typically closely mirrors those of their host. If a further reduction of CpG or UpA dinucleotide occurrence would further benefit expression of ORFs of viral genomes, then one would expect this to have occurred.

This is all the more relevant in the case of RNA viruses, in which the mutation rate is far higher than DNA viruses, because RNA polymerase lacks the proof-reading mechanism of DNA polymerases.

As touched on above, the current understanding of the mechanism though which CpG dinucleotides affect expression is that TLR9 receptors recognise unmethylated CpG dinucleotides in DNA molecules and induce the innate immune system. However, TLR9 does recognise ribonucleic acid CpG dinucleotides, and therefore this system would not have any effects on RNA-based expression vectors.

When one refers to the 'frequency' of a given dinucleotide, one is referring to the number of times it occurs in the relevant sequence. In a random sequence of sufficient length and equal frequencies of all 4 bases, one would expect any given dinucleotide to occur $1/16$th of the time as a result of chance, there being 16 possible dinucleotides. As discussed above, in real world situations, the normal frequency of any given dinucleotide in a given sequence is not random, because there are various pressures (some known, others not) acting upon the sequence composition. Thus, the actual frequency of a given dinucleotide varies from the expected frequency; in the case of CpG and UpA in mammalian or plant genomes, it is typically reduced. The present invention is concerned with reducing the frequency of CpG and/or UpA dinucleotides below their normal frequency (i.e. the frequency with which they occur in their normal context) to improve expression.

'Normal frequency' in the context of the present invention refers to the frequency of occurrence of CpG or UpA in an unmodified sequence, typically a wild type sequence. For example, in the case of a gene, the number of CpG or UpA dinucleotides in the synthetic nucleic acid according to the present invention would be fewer than the number of CpG or UpA dinucleotides in the wild type gene as it occurs in nature.

Preferably the frequency of CpG dinucleotides in the at least one region in which the nucleotide composition has been modified is reduced by at least 50%, i.e. if the normal sequence of interest contained 100 CpG dinucleotides, then it is preferred that the modified sequence contains 50 CpG dinucleotides or fewer.

Preferably the frequency of UpA dinucleotides in the at least one region in which the nucleotide composition has been modified is reduced by at least 50%, i.e. if the normal sequence of interest contained 100 UpA dinucleotides, then it is preferred that the modified sequence contains 50 UpA dinucleotides or fewer.

Preferably the frequency of both CpG and UpA dinucleotides in the at least one region in which the nucleotide composition has been modified is reduced by at least 50%.

More preferably the frequency of CpG and/or UpA dinucleotides in the at least one region reduced by at least 60%, more preferably 70%, 75%, 80%, 85%, 90%, 95% or 100%.

In a particularly preferred embodiment of the present invention the frequency of CpG and/or UpA dinucleotides in the at least one region in which the nucleotide composition has been modified has been modified such that it contains no CpG and/or UpA dinucleotides.

Considering the synthetic RNA expression vector as a whole, it is preferred that the frequency of CpG and/or UpA dinucleotides is reduced by at least 20%, more preferably at least 30%, 50%, 60% 70%, 80% or even 90% or higher.

Preferably the reduction of the frequency of CpG and/or UpA dinucleotides is achieved through the introduction of substitutions in the relevant region that do not influence its protei coding (synonymous substitutions).

Given the degeneracy of the genetic code, it is typically possible to reduce CpG content to zero in coding sequences without altering the encoded amino acid sequence, i.e. by synonymous substitution. For UpA the restriction that UpAp (U/C) codons encode tyrosine often precludes elimination of all UpA dinucleotides without alteration of the encoded amino acid sequence; in some cases it may be possible to work around this by altering the sequence to introducing a similar amino acid—depending on the context tyrosine can be substituted by other aromatic amino acids, in particular phenylalanine is in many ways chemically similar, although it lacks the hydroxyl group of tyrosine.

Suitably the frequency ratio of the relevant dinucleotide (i.e. CpG or UpA dinucleotides) is 0.4 or lower, preferably 0.3 or lower, more preferably 0.2 or lower, and most preferably 0.1 or lower in the synthetic RNA expression vector as a whole. For the avoidance of doubt, the 'frequency ratio' is defined as the ratio of observed dinucleotide frequency to the expected frequency based on mononucleotide composition (i.e. f(CpG)/f(C)*f(G)). The wild type frequency ratio for each of GpG and UpA is typically around 0.4 in vertebrates and 0.5 among RNA viruses which infect them.

In a preferred embodiment, the region of nucleic acid with reduced frequency of CpG or UpA dinucleotides is in a sequence which encodes an expression product. It is thus preferred that the nucleic acid with reduced frequency of CpG and/or UpA dinucleotides is an open reading frame (ORF).

Thus, it is typically preferred that the region or regions of the synthetic RNA expression vector in which the frequency of CpG and/or UpA dinucleotides have been reduced are coding regions of the vector of the present invention.

However, it is within the scope of the present invention that frequency of CpG and/or UpA dinucleotides is reduced in regions other than coding regions. Thus, the frequency of CpG and/or UpA dinucleotides can be reduced in non-coding regions. It is typically important that, where regions outside of ORFs are altered to remove CpG and/or UpA dinucleotides, the alterations do not adversely affect the vector. For example, alterations in sequences responsible for replication, such as translation, transcription or replication elements, could lead to a loss of replication competency. Alternatively, alterations in expression control sequences could adversely affect expression of an expression product.

Another situation where it may be problematic to remove CpG and/or UpA dinucleotides is in sequences with overlapping ORFs. An overlapping ORF is where a given sequence codes for more than one expression product (e.g. a protein), but where each expression product is in a different reading frame (i.e. offset by one or two positions). This situation is uncommon other than in viruses where there is pressure to maximise coding capacity of the genome. In the case of overlapping ORFs care must be taken that alterations to reduce the CpG and/or UpA content do not inadvertently disrupt the second reading frame. Of course, if only the expression product of the first reading frame is of interest then it would not matter if the second reading frame was abrogated.

It is typically most preferred that substantially all of the coding regions of the synthetic RNA expression vector have been modified to have a reduced CpG and/or UpA dinucleotide frequency. However, where there are overlapping ORFs or other features which constrain the possibility of making silent changes to sequence in some regions, it is preferred that in all other coding regions are modified.

The term 'non-constrained coding sequences' can be used to refer to all sequences which are not constrained in terms of modifying their sequence through synonymous substitutions, e.g. because of overlapping ORFs. Thus, in preferred embodiments, substantially all non-constrained coding sequences of the vector have been modified to reduce the frequency of CpG and/or UpA dinucleotides.

Preferably, regions totalling at least 50% of the total length of the synthetic RNA expression vector have been modified to reduce the CpG and/or UpA dinucleotides frequency. More preferably regions totalling at least 60% of the total length of the synthetic RNA expression vector have been modified, yet more preferably at least 70%.

It has been observed that enhancement of expression is generally dose dependent, with increased reduction of CpG and/or UpA dinucleotides frequency resulting in a corresponding increase in expression. Thus, it is typically preferred that reduction of CpG and/or UpA dinucleotides frequency is maximised. This can be achieved in two ways, 1) maximising the proportion of the total sequence length in which the CpG and/or UpA dinucleotides frequency is reduced, and 2) maximising the extent to which CpG and/or UpA dinucleotides frequency is reduced in those regions. Preferably both 1) and 2) of these are maximised in order to optimise expression.

Where the synthetic RNA expression vector comprises a sequence encoding a reporter expression produce (e.g. luciferase), it is preferred that this sequence also has reduced frequency of CpG and/or UpA dinucleotides.

In a particularly preferred embodiment of the present invention, the region having reduced frequency of CpG and/or UpA dinucleotides comprises a sequence of viral origin. More preferably it is a viral ORF. In a particularly preferred embodiment it is derived from a viral genome.

In a particularly preferred embodiment the synthetic RNA expression vector is a recombinant genome of an RNA virus. An RNA virus can be defined as any virus with a genome formed of RNA and which does not include a DNA intermediate as part of its life cycle. Examples of RNA viruses include influenza viruses, hepatitis C virus, SARS coronavirus, poliovirus, measles virus and West Nile virus. RNA viruses can also be defined as those that belong to groups III, IV or V of the Baltimore classification system of classifying viruses.

Preferably the virus is a virus which infects humans. Alternatively the virus is a virus which infects non-human animals, for example such as pigs, cattle, horses, dogs, cats, birds or sheep.

In preferred embodiments of the present invention the synthetic RNA expression vector comprises a recombinant single stranded RNA (ssRNA) virus genome. Suitably the synthetic RNA expression vector comprises a recombinant negative sense ssRNA virus genome, e.g. any virus from Group V. Alternatively, the synthetic RNA expression vector comprises a recombinant positive sense ssRNA virus genome, e.g. any virus from Group IV.

In alternative embodiments, the synthetic RNA expression vector comprises a recombinant double stranded (dsRNA) virus genome, e.g. any virus from Group III.

In a particularly preferred embodiment the synthetic RNA expression vector comprises a RNA virus adapted for expression in a suitable expression system for the production of a virus vaccine. Production of such RNA virus vaccines typically involved production of a replication competent virus, followed by its inactivation prior to use as a vaccine. Commonly used inactivated human RNA virus vaccines have been developed for poliovirus, influenza A and B viruses, hepatitis A virus, hepatitis E virus, rabies virus and tick-borne encephalitis virus. Thus these virus vaccines are particularly suited for use in the present invention.

However, the invention can of course be applied to any modified RNA virus used for vaccination, for example for veterinary use.

In one highly preferred embodiment of the present invention the synthetic RNA expression vector comprises a recombinant influenza A virus genome with reduced and CpG and UpA dinucleotide frequencies.

In another embodiment of the present invention, the synthetic RNA expression vector comprises a recombinant echovirus genome in which coding regions have been modified to reduce CpG and/or UpA (preferably both) dinucleotide frequencies. In one particular example, there is provided an echovirus 7 genome in which wild type region 1 and/or region 2 (as defined below) have been modified to reduce CpG and/or UpA (preferably both) dinucleotide frequencies. For example, regions 1 and or 2 can be modified by replacing the wild type sequence with SEQ ID NOS 3 to 8 described below, as appropriate. In particular, SEQ ID NOS 7 and 8 can be inserted to replace the wild type sequences.

In a further aspect of the present invention there is provided a virion comprising a synthetic RNA expression vector as defined above. Preferably the virion is capable if infecting a suitable host cell. The virion comprises the synthetic RNA expression vector and viral proteins coat proteins. The virion may further comprise an envelope.

Suitably the virion is an RNA viral vaccine. Viral vaccines expressing heterologous pathogen antigens can be used as vaccines against these pathogens, based on the same rationale as DNA vaccines. Viral vaccines comprise a modified viral genome adapted to produce one or more antigens from a given pathogen. The viral vaccine is delivered to the cells of the body, where the antigen is expressed. Because the antigens are recognised as foreign, when they are processed by the host cells and displayed on their surface, this stimulates a range of immune responses. In such viral vaccines it is desirable to maximise expression of the antigen, and thus the present invention is highly relevant.

In many embodiments of the invention, the synthetic RNA expression vector or virion of the present invention is in isolated form. The term "isolated" means a biological component (such as a nucleic acid molecule or protein) that has been substantially separated or purified away from other biological components in the cell of the organism in which the component naturally occurs, i.e., other chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids, proteins and peptides.

The term 'purified' does not require absolute purity; rather, it is intended as a relative term. Thus, for example, a purified form is one in which the vector or virion is more enriched than the vector or virion is in its environment within a cell, such that the peptide is substantially separated from cellular components (e.g. lipids, carbohydrates, other nucleic acids and other polypeptides) that may accompany it. In another example, a purified preparation is one in which the vector or virion is substantially free from contaminants. In one example, a vector or virion of the disclosure is purified when at least 50% by weight of a sample is composed of the vector or virion, for example when at least 60%, 70%, 80%, 85%, 90%, 92%, 95%, 98%, or 99% or more of a sample is composed of the vector or virion.

A 'recombinant' or 'synthetic' nucleic acid is one that has a sequence that is not naturally occurring and/or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Suitable techniques are set out in Green & Sambrook, Molecular Cloning: A Laboratory Manual (Fourth Edition), 2012, Cold Spring Harbor Laboratory Press.

In a further aspect the present invention provides a host cell comprising a synthetic RNA expression vector as defined above.

Preferably the cell is a eukaryotic cell, more preferably an animal cell, more preferably a mammalian cell. Suitable host cells will depend on the nature of the vector, especially the regulatory sequences is contains.

In a further aspect the present invention provides a clonal cell population derived from the host cell described above.

In another aspect the present invention provides an egg comprising cells which comprise a synthetic RNA expression vector as defined above.

Suitably the egg is an avian egg, more preferably a chicken egg. For example, the present invention provides an avian egg inoculated with a synthetic RNA expression vector as defined above, which encodes an RNA virus, e.g. an influenza virus.

In another aspect the present invention provides an expression system comprising cells comprising a synthetic RNA expression vector as defined above, and a suitable growth medium.

In a further aspect, the present invention provides an RNA virus vaccine composition, the composition comprising a virion which comprises a synthetic RNA expression vector as defined above, the vector comprising a sequence encoding one or more antigens. The antigen is preferably heterologous, i.e. it is derived from (and intended to raise immunity against) a pathogen which is different from the virus from which the synthetic RNA expression vector or the virion proteins are derived. Suitably the RNA virus vaccine composition comprises a pharmaceutically acceptable carrier, excipient or adjuvant. The RNA virus vaccine composition is preferably formulated for delivery to a subject in need of vaccination, e.g. an animal. Delivery can suitably be via oral or parenteral routes. Actual methods for preparing administrable compositions, whether for intravenous or subcutaneous administration or otherwise, will be known or apparent to those skilled in the art and are described in more detail in such publications as Remington's Pharmaceutical Science, 19th ed., Mack Publishing Company, Easton, Pa. (1995).

In another aspect the present invention provides a method of producing a synthetic RNA expression vector, the method comprising:

- providing a primary nucleotide sequence of interest (e.g. a gene, an ORF or a portion thereof);
- identifying at least one region of said primary nucleotide sequence susceptible to modification to reduce the frequency of CpG and/or UpA dinucleotides;
- identifying one or more sequence modifications in said at least one region which will reduce the frequency of CpG and/or UpA dinucleotides;
- providing a modified nucleotide sequence comprising some or all of said sequence modifications;
- producing a synthetic RNA expression vector comprising said modified sequence which has a reduced frequency of CpG and/or UpA dinucleotides compared to a corresponding (i.e. otherwise identical) synthetic RNA expression vector which comprises the primary nucleotide sequence.

Suitably manipulation of sequences (e.g. assembly of component parts of an expression vector) can be performed in a DNA 'intermediate', for subsequent transcription into an RNA form. Manipulation of DNA is typically much more straightforward than direct manipulation of RNA, and thus the present invention contemplates the use of DNA polynucleotides as 'working' molecules where required. References to 'reducing the frequency of CpG and UpA nucleotides' should thus be understood as including corresponding changes in the DNA intermediates (which of course will not include uracil) which result in a reduction in frequency in the RNA end product. An exemplary methodology using a DNA intermediate is described in detail below in respect of E7, and similar techniques for other viral vectors would be apparent to the skilled person. Accordingly, the method may comprise preparing a DNA polynucleotide which encodes a synthetic polynucleotide having a reduced CpG and/or UpA frequency. It may also comprise the step of transcribing said DNA polynucleotide to form a synthetic RNA polynucleotide having a reduced CpG and/or UpA frequency.

Modification of the sequence will typically involve making synonymous substitutions, which do not change the encoded amino acid sequence, but in some cases may involve making an alteration which results in a conservative amino acid substitution, as is discussed in more detail above. In silico methods for identifying suitable sequence changes are preferred.

According to another aspect of the present invention there is provided a method of producing an expression product, the method comprising:
  providing a host cell comprising a synthetic RNA expression vector as defined above;—incubating said cell under suitable conditions to induce expression from the vector; and
  recovering the expression product.

Suitably the expression product comprises a modified or wild type viral protein.

Suitably the expression product is a virion.

Suitably the method includes the following steps:
  providing an RNA sequence encoding an expression product;
  altering the nucleotide composition of said sequence to reduce the frequency of CpG and/or UpA dinucleotides; and
  introducing a synthetic RNA expression vector comprising said nucleic acid into a host cell.

The method may comprise transducing a cell with the synthetic RNA expression vector. This is of course particularly relevant where the synthetic RNA expression vector is comprised in a virion which is able to infect the cell.

In a preferred embodiment the method is a method for production of a viral vaccine. Such a method suitably comprises providing a virion comprising a synthetic RNA expression vector as defined above, introducing said synthetic RNA expression vector to a cell (e.g. in egg culture), incubating said cell under suitable conditions to produce viral proteins and thereby allow replication of the virion in the cell, and then inactivating the virion prior to use as a vaccine.

The method may suitably involve at least partially purifying the virion thereby produced.

In certain embodiments, the method can comprise a method of increasing the rate of replication of a synthetic virus within a host system by reducing the frequency of CpG and UpA dinucleotides in the virus compared with normal frequency.

In a further aspect the present invention provides a synthetic RNA expression vector as set out above for use in a method of treating or immunising against a disease.

In this aspect the synthetic RNA expression vector can be in the form of a viral vaccine.

In a further aspect the present invention provides a method of treating or preventing a disease by administering a pharmaceutical composition comprising the synthetic RNA expression vector as set out above (e.g. as a viral vaccine).

Luminescence was measured relative to the mock-transfected control. Results are the mean and standard error of three biological replicates.

Figure 6:
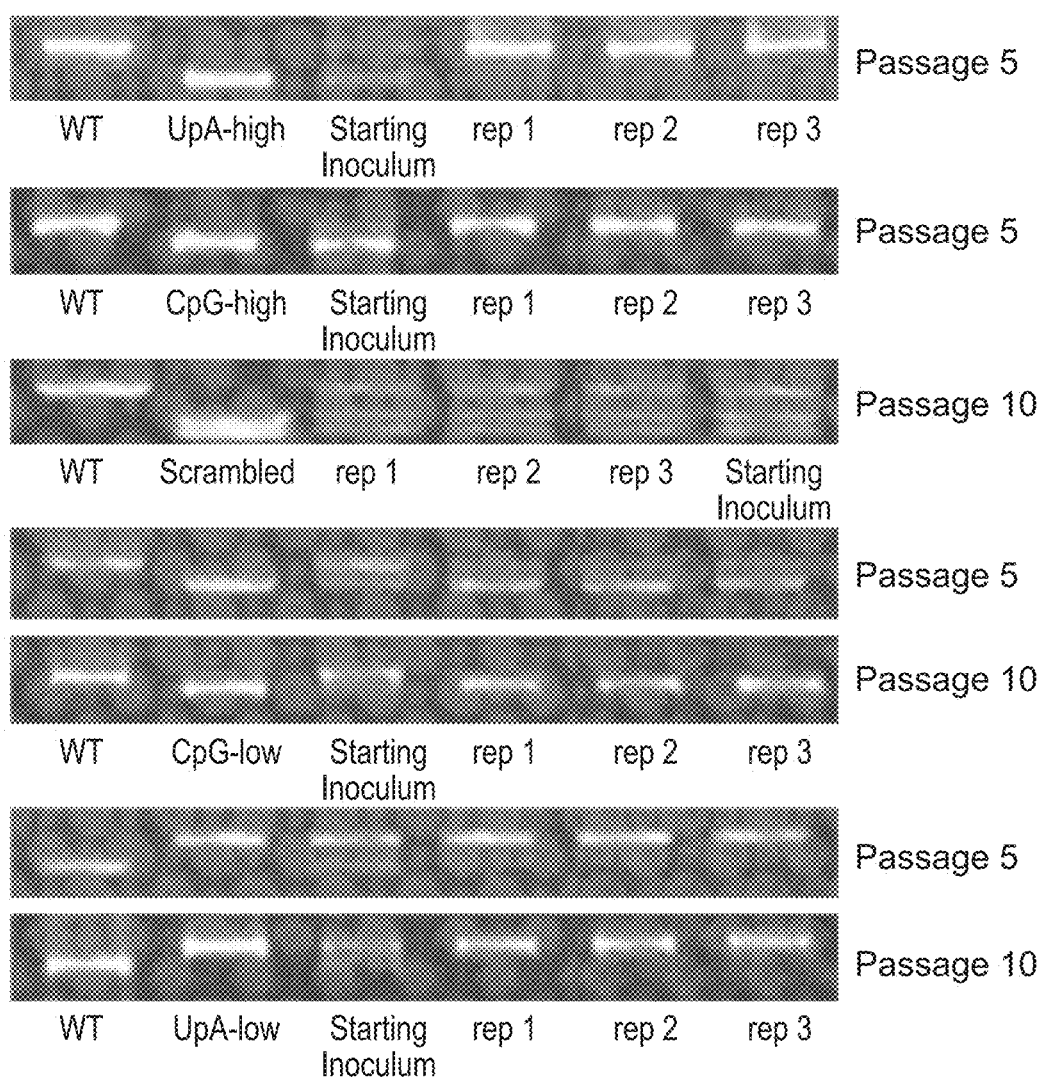

FIG. 6. Fitness determination by competition assays between WT and modified viruses. Cells were infected with an equal MOI of WT and modified virus, and the supernatant serially passaged through cells. RNA was isolated and the composition of each virus determined through selective restriction digest (enzymes used are given in Table 2).

Images show the virus composition in the starting inoculum and in three biological replicates following passage.

Figures 7A, 7B:
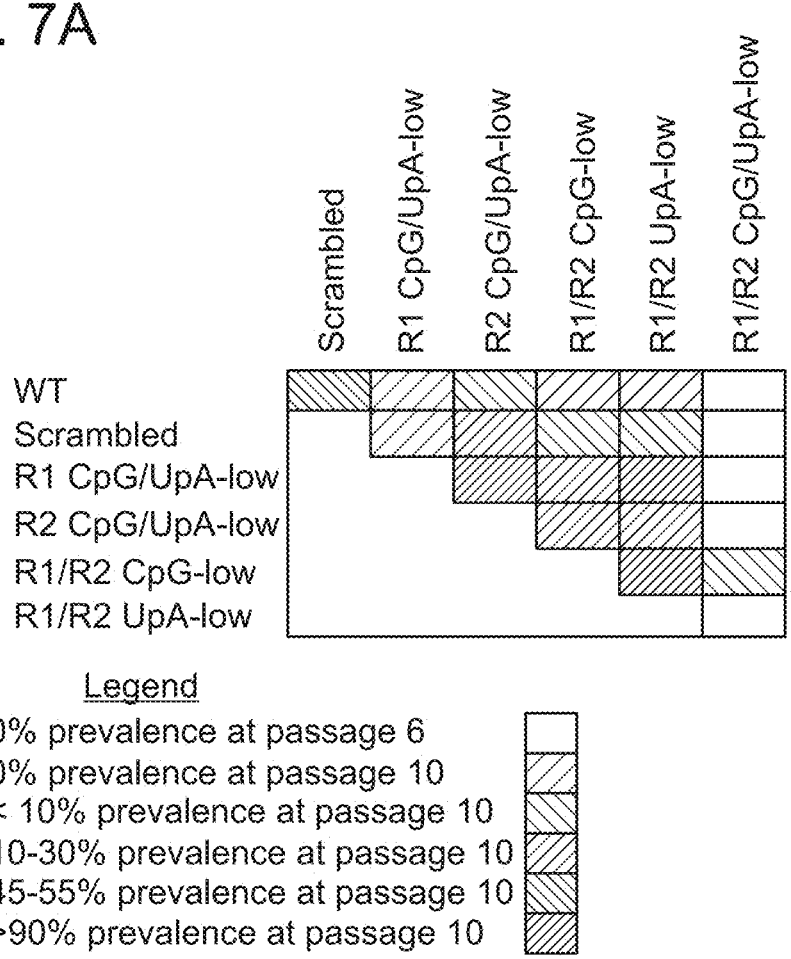

FIG. 7A-B. Pairwise fitness comparison between CpG-low and UpA-low viruses. Cells were infected with an equal MOI of two viruses and the supernatant serially passaged. The composition of each virus was determined through selective digest, and is displayed by differential shading (A). The more rapidly the virus on the left out-competed the virus shown above, the darker the shading. A fitness ranking was then determined (B).

Figure 8:
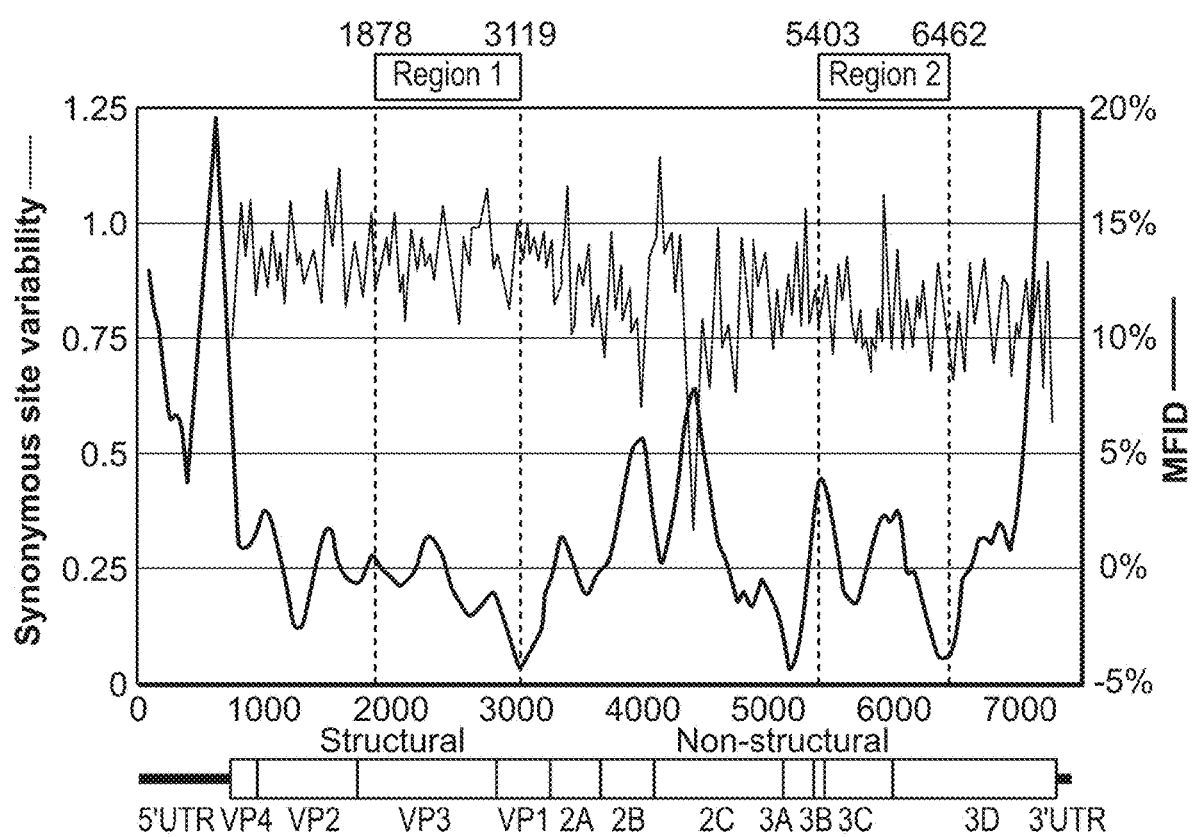

FIG. 8. Genome organisation of E7 and positions of mutated insert regions. Insert positions are compared to genome diagram and a plot of sequence variability within species B at synonymous sites (dotted line) and folding energies indicative of RNA secondary structure (solid line). Variability at synonymous sites (left y-axis) was computed at each codon position in alignments, plotted with a window size of 41 codons. MFED values (right y-axis) for sense and antisense RNA sequences were calculated for 200 base fragments, incrementing by 48 bases; values plotted represent mean values of 5 consecutive fragments. Nucleotide positions were calculated relative to the pT7:e7 clone sequence.

Figure 9:
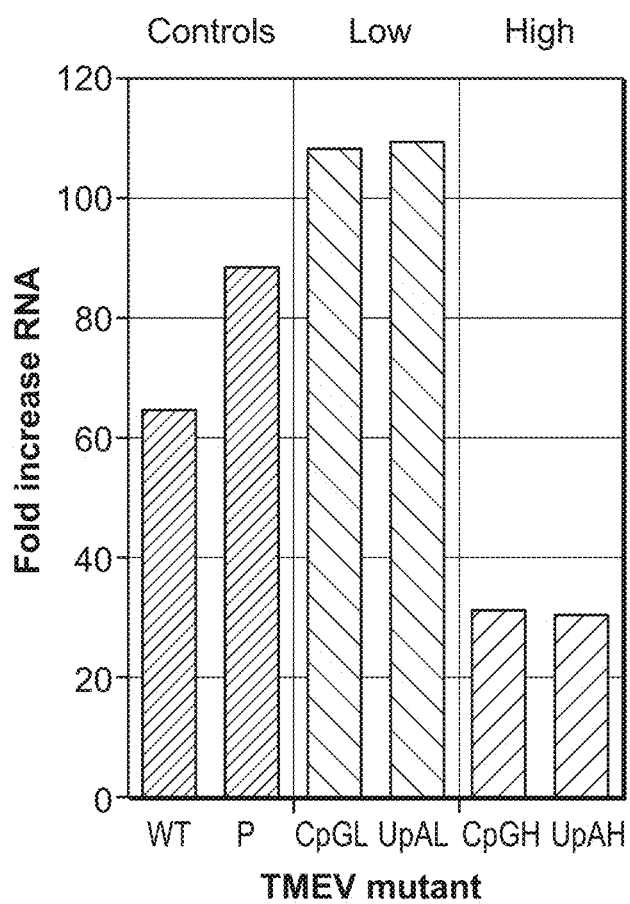

FIG. 9. Effect of CpG and UpA frequency changes on the replication of TMEV in mouse RAW cells. Removal of CpG and UpA dinucleotides in non-structural gene region of the genome led to enhancement of replication as determined by quantitative PCR of TMEV RNA sequences at 24 hours post-infection (y-axis scale). Conversely, addition of CpG and UpA dinucleotides in this genome region suppressed replication. The degree of replication enhancement and attenuation was comparable to that observed in mutants of echovirus 7 with similar extents of sequence replacement (single genome regions; Atkinson et al. 2014, Nucleic acids research, gku075).

Figure 10:
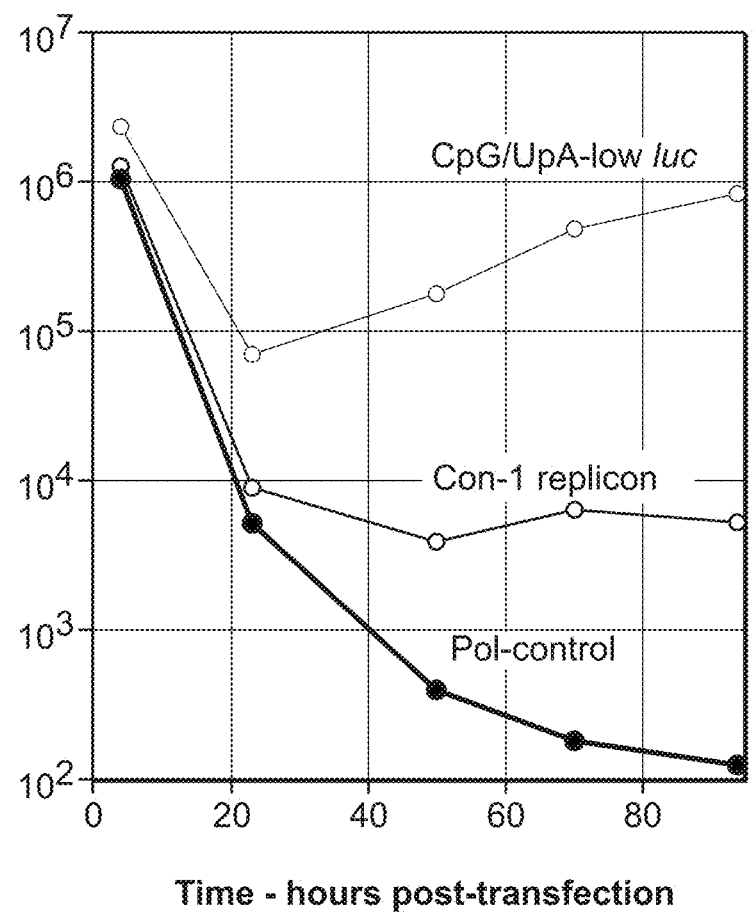

FIG. 10. Effect of CpG and UpA reduction in the luciferase gene on gene expression and replication of the HCV replicon. Removal of CpGs and UpAs enhanced luciferase expression immediately post-transfection and accelerated replication relative to the unmodified Con-1 replicon for at least 96 hours. Pol- is the non-replicating control RNA (mutated GDD→GND motif in RNA polymerase).

Figure 11:
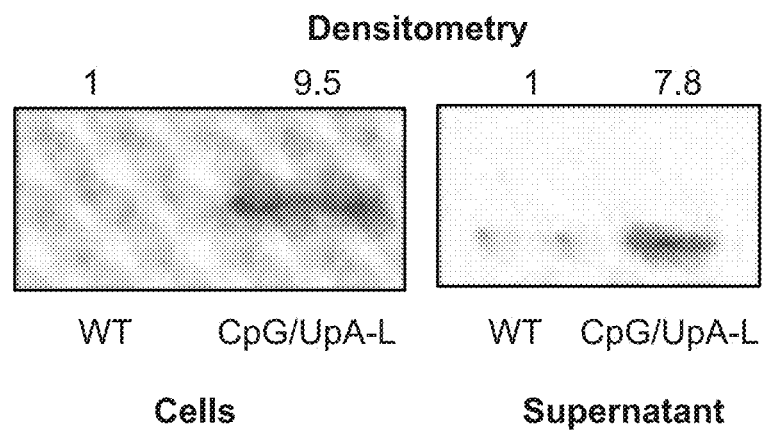

FIG. 11. Quantitation of capsid protein synthesis by Western blot of protein extracted from cells and cell free supernatant at 18 hours after infection with wild type (WT) or CpG/UpA-low mutants of E7 (moderate cytopathic effect). Viral proteins were detected using a VP1-specific monoclonal antibody (DAKO, Clone 5-D8/1) and levels compared by densitometry (values shown above panels, standardised to wild-type levels).

DETAILED DESCRIPTION

Materials and Methods Cell culture and cell lines E7 was propagated in rhabdomyosarcoma (RD) cells using Dulbecco modified Eagle medium (DMEM) with 10% foetal calf serum (FCS), penicillin (100 U/ml) and streptomycin (100 μg/ml). All cells were maintained at 37° C. with 5% $CO_2$.

In Silico Design of CpG and UpA Modified Viruses.

Two regions of the full length E7 cDNA pT7: E7 clone were selected for mutagenesis that lay in regions of the genome bounded by unique restriction sites SalI (genome position 1878) and Hpa\ (genome position 31 19) for Region 1 and EcoRI (genome position 5403) and BglII (genome position 6462) for Region 2. To generate CpG-low mutants, all CpG dinucleotides were eliminated by replacement of either the C or the G base with a randomly alternative selected base selected to preserve coding of the underlying sequence. A similar strategy was used to generate UpA-low mutants, with the restriction that UpAp(C or U) codons encoding tyrosine precluded elimination of all UpA dinucleotides. Introduction of as many possible CpG or UpA dinucleotides while preserving coding was employed to generate CpG-high and UpA-HIGH sequences. The sequence changes and base compositions of the resulting insert sequences are shown in Table 1.

TABLE 1

Composition of region 1 and 2 insert sequences

| Region | Sequence | G + C Content | freq$^a$ | CpG change$^b$ | ratio$^c$ | freq | UpA Change | Ratio |
|---|---|---|---|---|---|---|---|---|
| 1 | Native | 47.6% | 0.041 | — | 0.730 | 0.050 | — | 0.742 |
|   | Permuted | 47.6% | 0.041 | 0 | 0.730 | 0.050 | 0 | 0.742 |
|   | CpG-low | 44.3% | 0 | −51 | 0 | 0.057 | +8 | 0.741 |
|   | UpA-low | 50.6% | 0.045 | +5 | 0.703 | 0.015 | −43 | 0.256 |
|   | UpA/CpG-low | 47.5% | 0 | −51 | 0 | 0.015 | −43 | 0.227 |
|   | CpG-high | 56.5% | 0.146 | +129 | 1.828 | 0.042 | −10 | 0.900 |
|   | UpA-high | 40.9% | 0.032 | −12 | 0.756 | 0.139 | +109 | 1.593 |
| 2 | Native | 47.6% | 0.018 | — | 0.320 | 0.047 | — | 0.695 |
|   | Permuted | 47.6% | 0.018 | 0 | 0.320 | 0.047 | 0 | 0.695 |
|   | CpG-low | 44.3% | 0 | −18 | 0 | 0.047 | — | 0.695 |
|   | UpA-low | 50.6% | 0.021 | +3 | 0.331 | 0.014 | −34 | 0.229 |
|   | UpA/CpG-low | 47.5% | 0 | −18 | 0 | 0.014 | −34 | 0.215 |
|   | CpG-high | 56.5% | 0.133 | +116 | 1.667 | 0.037 | −10 | 0.824 |
|   | UpA-high | 40.9% | 0.015 | −3 | 0.390 | 0.149 | +103 | 1.633 |

$^a$Frequency of dinucleotide in insert region
$^b$Change in the number of dinucleotides (CpG or UpA) between mutated and original WT sequence
$^c$Ratio of observed dinucleotide frequence to that expected based on mononucleotide composition i.e. f(CpG/f(C) * f(G)

The specific sequences of the wild type (WT), CpG-low, UpA-low and CpG and UpA-low for each of regions 1 and 2 were as follows:

```
Echovirus 7 WT Region 1
                                    (SEQ ID NO 1)
GUCGACUCCGUGGUGCCCGUCAACAAUAUCAAAGUCAACCUGCAAAGCAU

GGAUGCGUAUCAUAUUGAGGUCAAUACCGGGAACCACCAGGGGGAAAAGA
```

-continued

UUUUUGCGUUCCAAAUGCAGCCGGGGUUAGAGUCUGUUUUCAAGAGAACC

CUUAUGGGGAGAUUCUUAAUUAUUAUGCACACUGGUCAGGGAGCAUUAA

GCUGACAUUCACAUUUUGUGGAUCGGCGAUGGCAACUGGAAAACUCUUGU

UAGCGUAUUCACCACCAGGUGCUGAUGUGCCCGCGACCAGGAAACAGGCG

AUGUUAGGCACACACAUGAUUUGGGAUAUCGGGCUUCAGUCGAGCUGUGU

UUUGUGCAUCCCAUGGAUAAGUCAGACACACUACCGGUUAGUGCAACAAG

AUGAAUACACGAGUGCAGGCAAUGUGACGUGUUGGUACCAAACAGGAAUA

GUGGUGCCCCCUGGCACUCCAAAUAAGUGUGUAGUGCUUUGUUUUGCAUC

AGCUUGUAAUGAUUUCUCAGUUCGAAUGCUUAGGGACACCCCUUUCAUCG

GACAAACAGCACUGCUGCAAGGCGACACCGAAACGGCUAUUGACAAUGCA

AUCGCCAGGGUAGCAGAUACGGUGGCGAGCGGUCCUAGUAAUUCGACCAG

UAUCCCAGCACUCACAGCAGUUGAGACAGGUCACACGUCACAAGUCGAGC

CCAGCGAUACAAUGCAGACUAGACAUGUCAAAAACUACCACUCGCGUUCU

GAGUCAACCGUGGAAAACUUUCUAAGUCGCUCCGCUUGUGUGUACAUCGA

AGAGUACUACACCAAGGACCAAGACAAUGUUAAUAGGUACAUGUCGUGGA

CAAUAAAUGCCAGAAGAAUGGUGCAAUUGAGGAGAAAGUUUGAGCUGUUU

ACAUACAUGAGAUUUGAUAUGGAAAUCACGUUUGUAAUCACAAGUAGACA

ACUACCUGGGACUAGCAUAGCACAAGAUAUGCCGCCACUCACCCACCAGA

UCAUGUACAUACCACCAGGUGGCCCGGUACCAAACAGCGUAACAGAUUUU

GCGUGGCAGACAUCAACAAACCCCAGCAUUUUCUGGACAGAAGGAAACGC

GCCACCUCGCAUGUCUAUUCCAUUCAUCAGUAUUGGCAAUGCAUAUAGCA

ACUUCUAUGACGGGUGGUCACACUUUUCCCAAAACGGUGUGUACGGAUAC

AACGCCCUGAACAACAUGGGCAAGCUGUACGCACGUCAUGUUAAC

Echovirus 7 WT Region 2

(SEQ ID NO 2)
GAAUUCGCCGUUGCUAUGAUGAAGAGAAACUCAAGUACAGUGAAGACUGA

GUAUGGUGAGUUUACUAUGCUGGGCAUCUAUGACAAGUGGGCCGUUUUGC

CACGCCAUGCUAAACCUGGACCAACCAUCCUGAUGAAUGACCAAGAGGUC

GGCGUGUUAGACGCCAAGGAACUAGUGGACAAGGAUGGCACUAACCUGGA

GCUGACACUACUCAAGUUAAACCGGAAUGAGAAGUUCAGAGACAUCAGAG

GCUUCUUGGCUAAGGAGGAAGUGGAAGUCAACGAGGCUGUGCUGGCAAUA

AACACUAGCAAGUUUCCUAACAUGUACAUUCCAGUAGGGCAGGUUACAGA

UUACGGCUUCCUAAACCUGGGGUGGUACACCCACCAAAAGAAUGCUUAUGU

AUAACUUCCCCACAAGAGCAGGCCAGUGUGGCGGGGUACUCAUGUCCACU

GGCAAAGUUUGGGAAUCCAUGUUGGUGGAAAUGGCCAUCAAGGCUUCUC

AGCAGCACUUCUCAAACACUACUUUAAUGAUGAACAAGGAGAGAUUGAGU

UCAUUGAGAGUUCAAAGGAAGCAGGGUUCCCAAUCAUUAACGCACCCAGU

AAAACCAAGCUGGAGCCAAGUGUCUUCCACCAAGUAUUUGAAGGCAACAA

AGAGCCAGCAGUCCUCAGGAACAGUGACCCACGUCUCAAAGCUAAUUUCG

AGGAGGCCAUCUUUUCCAAAUACAUUGGGAAUGUCAACACACACAUAGAU

GAAUACAUGUUGGAGGCUGUUGACCAUUAUGCCGGACAAUUGGCCACCCU

AGAUAUCAGCACUGAACCAAUGAAGUUGGAGGAUGCUGUGUACGGUACUG

-continued

AAGGCCUUGAAGCUCUUGACUUAACAACAAGUGCAGGCUACCCCUAUGUC

GCACUGGGUAUCAAGAAGAGAGACAUCCUCUCGAAGAAGACCAAGGACCU

GACCAAGCUGAAAGAGUGCAUGGAUAAGUAUGGCCUGAAUCUACCAAUGG

UGACAUACGUGAAGAUGAACUCAGAUCU

CpG-low Region 1

(SEQ ID NO 3)
GUCGACUCAGUGGUGCCAGUCAACAAUAUCAAAGUCAACCUGCAAAGCAU

GGAUGCUUAUCAUAUUGAGGUCAAUACAGGGAACCACCAGGGGGAAAAGA

UUUCUGCUUUCCAAAUGCAGCCUGGGUUAGAGUCUGUUUUCAAGAGAACC

CUUAUGGGGAGAUUCUUAAUUAUUAUGCACACUGGUCAGGGAGCAUUAA

GCUGACAUUCACAUUUUGUGGAUCUGCCAUGGCAACUGGAAAACUCUUGU

UAGCUUAUUCACCACCAGGUGCUGAUGUGCCUGCAACCAGGAAACAGGCU

AUGUUAGGCACACACAUGAUUUGGGAUAUAGGGCUUCAGUCCAGCUGUGU

UUUGUGCAUCCCAUGGAUAAGUCAGACACACUACAGGUUAGUGCAACAAG

AUGAAUACACAAGUGCAGGCAAUGUGACAUGUUGGUACCAAACAGGAAUA

GUGGUGCCCCCUGGCACUCCAAAUAAGUGUGUAGUGCUUUGUUUUGCAUC

AGCUUGUAAUGAUUUCUCAGUUAGGAUGCUUAGGGACACCCCUUUCAUAG

GACAAACAGCACUGCUGCAAGGAGACACAGAAACAGCUAUUGACAAUGCA

AUUGCCAGGGUAGCAGAUACUGUGGCAAGUGGUCCUAGUAAUUCAACCAG

UAUCCCAGCACUCACAGCAGUUGAGACAGGUCACACCUCACAAGUGGAGC

CCAGUGAUACAAUGCAGACUAGACAUGUCAAAAACUACCACUCUAGGUCU

GAGUCAACUGUGGAAAACUUUCUAAGUAGGUCAGCUUGUGUGUACAUGA

AGAGUACUACACCAAGGACCAAGAC

AAUGUUAAUAGGUACAUGUCCUGGACAAUAAAUGCCAGAAGAAUGGUGCA

AUUGAGGAGAAAGUUUGAGCUGUUUACAUACAUGAGAUUUGAUAUGGAAA

UCACCUUUGUAAUCACAAGUAGACAACUACCUGGGACUAGCAUAGCACAA

GAUAUGCCACCACUCACCCACCAGAUCAUGUACAUACCACCAGGUGGCCC

AGUACCAAACAGUGUAACAGAUUUUGCCUGGCAGACAUCAACAAACCCCA

GCAUUUUCUGGACAGAAGGAAAUGCCCCACCUAGGAUGUCUAUUCCAUUC

AUCAGUAUUGGCAAUGCAUAUAGCAACUUCUAUGAUGGGUGGUCACACUU

UUCCCAAAAUGGUGUGUAUGGAUACAAUGCCCUGAACAACAUGGGCAAGC

UGUAUGCAAGACAUGUUAAC

CpG-low Region 2

(SEQ ID NO 4)
GAAUUCGCUGUUGCUAUGAUGAAGAGAAACUCAAGUACAGUGAAGACUGA

GUAUGGUGAGUUUACUAUGCUGGGCAUCUAUGACAAGUGGGCAGUUUUGC

CAAGGCAUGCUAAACCUGGACCAACCAUCCUGAUGAAUGACCAAGAGGUU

GGGGUGUUAGAUGCCAAGGAACUAGUGGACAAGGAUGGCACUAACCUGGA

GCUGACACUACUCAAGUUAAACAGAAAUGAGAAGUUCAGAGACAUCAGAG

GCUUCUUGGCUAAGGAGGAAGUGGAAGUCAAUGAGGCUGUGCUGGCAAUA

AACACUAGCAAGUUUCCUAACAUGUACAUUCCAGUAGGGCAGGUUACAGA

UUAUGGCUUCCUAAACCUGGGGUGGUACACCCACCAAAAGAAUGCUUAUGU

-continued

AUAACUUCCCCACAAGAGCAGGCCAGUGUGGAGGGGUACUCAUGUCCACU

GGCAAAGUUUUGGGAAUCCAUGUUGGUGGAAAUGGCCAUCAAGGCUUCUC

AGCAGCACUUCUCAAACACUACUUUAAUGAUGAACAAGGAGAGAUUGAGU

UCAUUGAGAGUUCAAAGGAAGCAGGGUUCCCAAUCAUUAAUGCACCCAGU

AAAACCAAGCUGGAGCCAAGUGUCUUCCACCAAGUAUUUGAAGGCAACAA

AGAGCCAGCAGUCCUCAGGAACAGUGACCCAAGGCUCAAAGCUAAUUUUG

AGGAGGCCAUCUUUUCCAAAUACAUUGGGAAUGUCAACACACACAUAGAU

GAAUACAUGUUGGAGGCUGUUGACCAUUAUGCAGGACAAUUGGCCACCCU

AGAUAUCAGCACUGAACCAAUGAAGUUGGAGGAUGCUGUGUAUGGUACUG

AAGGCCUUGAAGCUCUUGACUUAACAACAAGUGCAGGCUACCCCUAUGUG

GCACUGGGUAUCAAGAAGAGAGACAUCCUCUCAAAGAAGACCAAGGACCU

GACCAAGCUGAAAGAGUGCAUGGAUAAGUAUGGCCUGAAUCUACCAAUGG

UGACAUAUGUGAAAGAUGAACUCAGAUCU

UpA-low Region 1

(SEQ ID NO 5)

GUCGACUCCGUGGUGCCCGUCAACAACAUCAAAGUCAACCUGCAAAGCAU

GGAUGCGUAUCACAUUGAGGUCAACACCGGGAACCACCAGGGGGAAAAGA

UUUUUGCGUUCCAAAUGCAGCCGGGGUUGGAGUCUGUUUUCAAGAGAACC

CUCAUGGGGGAGAUUCUCAAUUAUUAUGCACACUGGUCAGGGAGCAUCAA

GCUGACAUUCACAUUUUGUGGAUCGGCGAUGGCAACUGGAAAACUCUUGU

UGGCGUAUUCACCACCAGGUGCUGAUGUGCCCGCGACCAGGAAACAGGCG

AUGUUGGGCACACACAUGAUUUGGGACAUCGGGCUUCAGUCGAGCUGUGU

UUUGUGCAUCCCAUGGAUCAGUCAGACACACUACCGGUUGGUGCAACAAG

AUGAAUACACGAGUGCAGGCAAUGUGACGUGUUGGUACCAAACAGGAAUU

GUGGUGCCCCCUGGCACUCCAAACAAGUGUGUCGUGCUUUGUUUUGCAUC

AGCUUGCAAUGAUUUCUCAGUUCGAAUGCUGAGGGACACCCCUUUCAUCG

GACAAACAGCACUGCUGCAAGGCGACACCGAAACGGCGAUUGACAAUGCA

AUCGCCAGGGUUGCAGACACGGUGGCGAGCGGUCCGAGCAAUUCGACCAG

CAUCCCAGCACUCACAGCAGUUGAGACAGGUCACACGUCACAAGUCGAGC

CCAGCGACACAAUGCAGACCAGACAUGUCAAAAACUACCACUCGCGUUCU

GAGUCAACCGUGGAAAACUUUCUCAGUCGCUCCGCUUGUGUGUACAUCGA

AGAGUACUACACCAAGGACCAAGACAAUGUCAACAGGUACAUGUCGUGGA

CAAUCAAUGCCAGAAGAAUGGUGCAAUUGAGGAGAAAGUUUGAGCUGUUC

ACAUACAUGAGAUUUGACAUGGAAAUCACGUUUGUCAUCACAAGCAGACA

ACUUCCUGGGACGAGCAUCGCACAAGACAUGCCGCCACUCACCCACCAGA

UCAUGUACAUCCCACCAGGUGGCCCGGUCCCAAACAGCGUCACAGAUUUU

GCGUGGCAGACAUCAACAAACCCCAGCAUUUUCUGGACAGAAGGAAACGC

GCCACCUCGCAUGUCCAUUCCAUUC

AUCAGCAUUGGCAAUGCAUACAGCAACUUCUAUGACGGGUGGUCACACUU

UUCCCAAAACGGUGUGUACGGAUACAACGCCCUGAACAACAUGGGCAAGC

UGUACGCACGUCAUGUUAAC

-continued

UpA-low Region 2

(SEQ ID NO 6)

GAAUUCGCCGUUGCCAUGAUGAAGAGAAACUCAAGCACAGUGAAGACUGA

GUAUGGUGAGUUCACGAUCCUGGGCAUCUAUGACAAGUGGGCCGUUUUGC

CACGCCAUGCCAAACCUGGACCAACCAUCCUGAUGAAUGACCAAGAGGUC

GGCGUGUUGGACGCCAAGGAACUGGUGGACAAGGAUGGCACAAACCUGGA

GCUGACACUCCUCAAGUUGAACCGGAAUGAGAAGUUCAGAGACAUCAGAG

GCUUCUUGGCGAAGGAGGAAGUGGAAGUCAACGAGGCUGUGCUGGCAAUC

AACACCAGCAAGUUUCCAAACAUGUACAUUCCAGUUGGGCAGGUCACAGA

UUACGGCUUCCUGAACCUGGGUGGGACACCCACCAAAAGAAUGCUCAUGU

ACAACUUCCCCACAAGAGCAGGCCAGUGUGGCGGGGUGCUCAUGUCCACU

GGCAAAGUUUUGGGAAUCCAUGUUGGUGGAAAUGGCCAUCAAGGCUUCUC

AGCAGCACUUCUCAAACACUACUUCAAUGAUGAACAAGGAGAGAUUGAGU

UCAUUGAGAGUUCAAAGGAAGCAGGGUUCCCAAUCAUCAACGCACCCAGC

AAAACCAAGCUGGAGCCAAGUGUCUUCCACCAAGUGUUUGAAGGCAACAA

AGAGCCAGCAGUCCUCAGGAACAGUGACCCACGUCUCAAAGCCAAUUUCG

AGGAGGCCAUCUUUUCCAAAUACAUUGGGAAUGUCAACACACACAUCGAU

GAAUACAUGUUGGAGGCUGUUGACCAUUAUGCCGGACAAUUGGCCACCCU

UGACAUCAGCACUGAACCAAUGAAGUUGGAGGAUGCUGUGUACGGCACUG

AAGGCCUUGAAGCUCUUGACUUGACAACAAGUGCAGGCUACCCCUAUGUC

GCACUGGGGAUCAAGAAGAGAGACAUCUUCUCGAAGAAGACCAAGGACCU

GACCAAGCUGAAAGAGUGCAUGGACAAGUAUGGCCUGAAUCUUCCAAUGG

UGACAUACGUGAAAGAUGAACUCAGAUCU

CpG & UpA-low Region 1

(SEQ ID NO 7)

GUCGACUCAGUGGUGCCAGUCAACAACAUCAAAGUCAACCUGCAAAGCAU

GGAUGCUUAUCACAUUGAGGUCAACACAGGGAACCACCAGGGGGAAAAGA

UUUUUGCUUUCCAAAUGCAGCCUGGGUUGGAGUCUGUUUUCAAGAGAACC

CUGAUGGGGGAGAUUCUGAAUUAUUAUGCACACUGGUCAGGGAGCAUCAA

GCUGACAUUCACAUUUUGUGGAUCUGCCAUGGCAACUGGAAAACUCUUGU

UGGCUUAUUCACCACCAGGUGCUGAUGUGCCUGCAACCAGGAAACAGGCC

AUGUUGGGCACACACAUGAUUUGGGACAUUGGGCUUCAGUCCAGCUGUGU

UUUGUGCAUCCCAUGGAUCAGUCAGACACACUACAGGUUGGUGCAACAAG

AUGAAUACACAAGUGCAGGCAAUGUGACAUGUUGGUACCAAACAGGAAUU

GUGGUGCCCCCUGGCACUCCAAACAAGUGUGUUGUGCUUUGUUUUGCAUC

AGCUUGCAAUGAUUUCUCAGUCAGGAUGCUCAGGGACACCCCUUUCAUUG

GACAAACAGCACUGCUGCAAGGAGACACAGAAACAGCCAUUGACAAUGCA

AUUGCCAGGGUUGCAGACACUGUGGCAAGUGGUCCAAGCAAUUCAACCAG

CAUCCCAGCACUCACAGCAGUUGAGACAGGUCACACCUCACAAGUGGAGC

CCAGUGACACAAUGCAGACAAGACAUGUCAAAAACUACCACUCCAGGUCU

GAGUCAACUGUGGAAAACUUUCUCAGCAGGUCAGCUUGUGUGUACAUUGA

AGAGUACUACACCAAGGACCAAGACAAUGUCAACAGGUACAUGUCCUGGA

CAAUCAAUGCCAGAAGAAUGGUGCAAUUGAGGAGAAAGUUUGAGCUGUUC

-continued

ACAUACAUGAGAUUUGACAUGGAAAUCACCUUCGUGAUCACAAGCAGACA

ACUCCCUGGGACAAGCAUUGCACAAGACAUGCCACCACUCACCCACCAGA

UCAUGUACAUUCCACCAGGUGGCCCAGUGCCAAACAGUGUCACAGAUUUU

GCCUGGCAGACAUCAACAAACCCCAGCAUUUUCUGGACAGAAGGAAAUGC

CCCACCAAGGAUGUCCAUUCCAUUCAUCAGCAUUGGCAAUGCAUACAGCA

ACUUCUAUGAUGGGUGGUCACACUUUUCCCAAAAUGGUGUGUAUGGAUAC

AAUGCCCUGAACAACAUGGGCAAGCUGUAUGCAAGACAUGUUAAC

CpG & UpA-low Region 2
(SEQ ID NO 8)
GAAUUCGCUGUUGCCAUGAUGAAGAGAAACUCAAGCACAGUGAAGACUGA

GUAUGGUGAGUUCACCAUGCUGGGCAUCUAUGACAAGUGGGCAGUUUUGC

CAAGGCAUGCCAAACCUGGACCAACCAUCCUGAUGAAUGACCAAGAGGUU

GGGGUGUUGGAUGCCAAGGAACUGGUGGACAAGGAUGGCACCAACCUGGA

GCUGACACUUCUCAAGUUGAACAGAAAUGAGAAGUUCAGAGACAUCAGAG

GCUUCUUGGCCAAGGAGGAAGUGGAAGUCAAUGAGGCUGUGCUGGCAAUC

AACACCAGCAAGUUUCCCAACAUGUACAUUCCAGUGGGGCAGGUGACAGA

UUAUGGCUUCCUGAACCUGGGUGGAACACCCACCAAAAGAAUGCUCAUGU

ACAACUUCCCCACAAGAGCAGGCCAGUGUGGAGGGGUUCUCAUGUCCACU

GGCAAAGUUUUGGGAAUCCAUGUUGGUGGAAAUGGCCAUCAAGGCUUCUC

AGCAGCACUUCUCAAACACUACUUCAAUGAUGAACAAGGAGAGAUUGAGU

UCAUUGAGAGUUCAAAGGAAGCAGGGUUCCCAAUCAUCAAUGCACCCAGC

AAAACCAAGCUGGAGCCAAGUGUCUUCCACCAAGUGUUUGAAGGCAACAA

AGAGCCAGCAGUCCUCAGGAACAGUGACCCAAGGCUCAAAGCCAAUUUUG

AGGAGGCCAUCUUUUCCAAAUACAUUGGGAAUGUCAACACACAUUGAU

GAAUACAUGUUGGAGGCUGUUGACCAUUAUGCAGGACAAUUGGCCACCCU

GGACAUCAGCACUGAACCAAUGAAGUUGGAGGAUGCUGUGUAUGGCACUG

AAGGCCUUGAAGCUCUUGACUUGACAACAAGUGCAGGCUACCCCUAUGUG

GCACUGGGGAUCAAGAAGAGAGACAUCCUCUCAAAGAAGACCAAGGACCU

GACCAAGCUGAAAGAGUGCAUGGACAAGUAUGGCCUGAAUCUCCCAAUGG

UGACAUAUGUGAAAGAUGAACUCAGAUCU

RNA structure prediction and sequence variability.

RNA Structure Prediction and Sequence Variability.

Prototype sequences of each species B serotype (http://www.picornaviridae.com/) were scanned for RNA secondary structure using the program Folding Energy Scan in the SSE package (Simmonds. 2012, BMC research notes 5: 50-50) using 200 base fragments incrementing by 152 bases and 50 sequence order randomised control using the algorithm NDR that preserves dinucleotide frequencies of the native sequence (Simmonds et al. 2004, RNA-Publ. RNA Soc. 10: 1337-1351). Mean MFED values for each fragment were plotted against the mid-point of each fragment to localise areas of sequence-order dependent RNA secondary structure. MFEDs were also similarly calculated for the reverse complement of each genome sequence. Synonymous sequence variability was determined by measurement of mean pairwise distances using the program Sequence Scan in the SSE package.

Clone Construction and Recovery of Mutant Viruses

The full length E7 cDNA pT7:E7 clone under the control of a T7 promoter was used for this study. Mutant E7 constructs with altered CpG/UpA content were generated by ordering custom DNA sequences (GeneArt, Life Technologies, Paisley, UK). Sequences were provided in standard antibiotic resistant cloning vectors and were cloned into pT7:E7 All clones were sequenced over the insert regions prior to further applications. To recover the mutant viruses with altered CpG/UpA content, assembled plasmids were linearised using NotI and a T7 transcription reaction carried out to create RNA using a Mega Script T7 in vitro transcription kit (Ambion). 100 ng of RNA was transfected into RD cells using Lipofectamine 2000 (Invitrogen) according to the manufacturer's instructions. The resulting cell lysates were used to generate passage 1 stocks by re-infecting RD cells. Viral titres were determined by $TCID_{50}$ titration in RD cells.

Replication Phenotype

RD cells were seeded at $5 \times 10^5$ cells per well in 6-well plates and subsequently infected with the WT or CpG/UpA mutants at an MOI of 0.01 per cell for 1 hour, before removing the inoculum and washing the cells. Samples were then withdrawn at given time points (12, 18, 24, 30, 42 hours post-infection) and the viral titre determined by $TCID_{50}$. The assay was performed in triplicate per virus. For plaque assays, confluent RD cells in 100 mm dishes or 6-well plates were inoculated with virus in DMEM and incubated for 1 hour at 37° C. with occasional rocking. The inoculum was removed and replaced with overlay consisting of 2% Methocel MC (Sigma) in DMEM. Plates were incubated for 96 hours at 37° C., fixed with 3.5% formaldehyde and stained with 0.1% crystal violet. Plaque sizes were quantified using ImageJ software.

Quantification of Viral RNA in Infected Cells

Load of viral RNA in infected RD cells was analysed using qRT-PCR. RNA was isolated from cells using the RNAspin Mini Kit (GE Healthcare) or from viral supernatant using the QIAamp Viral RNA Mini Kit (Qiagen). Reverse transcription was performed using M-MLV reverse transcriptase (Promega) and random primers. E7 cDNA was then quantified by qRT-PCR using primers annealing to the 5' UTR region (Sense: TCCGGCCCCTGAATGCGGCTAA (SEQ ID NO 9), Antisense: CACC-CAAAGTAGTCGGTTCCGC (SEQ ID NO 10)). Reactions were carried out using a Sensifast SYBR Mi-Rox Kit (Bioline) and a Rotorgene-Q cycler (Qiagen), and cycling conditions were as follows: 95° C. for 2 minutes, then 40 cycles of 95° C. for 5 seconds, 60° C. for 10 seconds and 72° C. for 20 seconds. A standard curve for E7 RNA using a quantified PCR product was carried out in parallel, allowing quantification of viral copy number. RNA to infectivity ratio was determined by extracting RNA from 5000 $TCID_{50}$ units per virus and by performing quantitative RT-PCR against a standard curve.

Replicon Construction and Replication Kinetics

To accurately quantify intracellular viral replication, the pRiboE7luc replicon plasmid was used. This contains a version of the E7 genome in which the structural genes (nucleotides 753 to 3118) are replaced with the 1704 bp-long firefly luciferase gene. In order to minimise frequencies of CpG and UpA dinucleotides within the luciferase gene, an alternative luciferase gene was designed using the same method as that described for Regions 1 and 2, and ordered as a custom DNA sequence. As before, the amino acid sequence remained unchanged. The custom luciferase gene also contained a CpG- and UpA-low 72 bp linker sequence at the 3' end to allow cloning into the SanDI restriction site at nucleotide 3191 of the E7 genome. The sequence was cloned into pT7:E7 using the unique restriction sites KasI (genome position 781) and SanDI. To create replicons containing the additional Region 2 CpG or UpA low inserts, a 3235 bp section of the replicon directly 3' of the luciferase gene was excised using SanDI and BglII restriction enzymes. This was then replaced with the equivalent sections of the previously described R1/R2 CpG low or R1/R2 UpA low constructs, containing the modified Region 2 inserts. Replicon plasmids were linearised using NotI and RNA was created in a T7 reverse transcription reaction.

Assays were performed by transfecting 50 ng of replicon RNA into RD cells seeded at 3×10⁴ cells per well in 96-well plates. RNA was transfected at given time points (1, 4, 6, 8, 12 hours) before luciferase assays were carried out using the Luciferase Assay System (Promega), according to the manufacturer's instructions. Cells were lysed using the Passive Lysis Buffer and the cell lysate transferred to opaque 96-well plates for luminescence analysis using the Glomax Multi Detection System (Promega).

Sequencing of Individual Virus Genomes

Viral RNA was isolated from E7 WT, R1/R2 CpG-high, or R1/R2 UpA-high virus stocks generated in RD cells, and cDNA created. Nested primers were designed to amplify a ~500 bp section of the modified Region 1 (nucleotides 1835-2363) and an unmodified region of E7 (nucleotides 3241-3723). Primer sequences are given in Table 2. The proofreading enzyme PfuTurbo DNA Polymerase (Agilent)) was used to amplify the two sections from each cDNA. The products were purified, cloned into a TA vector (pGEM-T easy, Promega), and transformed into competent *E. coli*, generating a separate colony for each copy of the original viral cDNA. The 500 bp inserts were sequenced using M13 primers.

TABLE 2

Nested primers used in sequencing individual viral genomes

| Region | Virus | Primer type | Nucleotide position | Sequence |
|---|---|---|---|---|
| 1 | All | Outer, sense | 1809 | CCCAATTTGATGTAACACCACACATGG SEQ ID NO 11 |
| 1 | All | Inner, sense | 1835 | GATATTCCAGGCGAAGTACACAACC SEQ ID NO 12 |
| 1 | EV7 WT | Outer, antisense | 2343 | CAAAGCACTACACACTTATTTGGAG SEQ ID NO 13 |
| 1 | R1/R2 CpG-high | Outer, antisense | 2382 | ATTCGAACGGAGAAATCGTTAC SEQ ID NO 14 |
| 1 | R1/R2 UpA-high | Outer, antisense | 2388 | TCCCTTAGCATACGTACTGAGAAAT SEQ ID NO 15 |
| 1 | EV7 WT | Inner, antisense | 2313 | GCACCACTATTCCTGTTTGGT SEQ ID NO 16 |
| 1 | R1/R2 CpG-high | Inner, antisense | 2348 | AACAAAGCACGACGCACTTATT SEQ ID NO 17 |
| 1 | R1/R2 UpA-high | Inner, antisense | 2363 | CATTACAAGCTGATCCAAAACATAG SEQ ID NO 18 |
| Unmodified | All | Outer, sense | 3210 | TGAGCCCGTACATCAAATCA SEQ ID NO 19 |
| Unmodified | All | Inner, sense | 3241 | TTTTAACCCCACGAACCTGA SEQ ID NO 20 |
| Unmodified | All | Outer, antisense | 3785 | TTGCCGAGTTGTTCGACATA SEQ ID NO 21 |
| Unmodified | All | Inner, antisense | 3723 | CAAGTCACGGATGTCTGCAA SEQ ID NO 22 |

Competition Assays

Equal titres of wild type (WT) and mutant virus (MOI=0.01) were applied simultaneously to RD cells in 24-well plates. Following CPE, the supernatant was frozen, thawed, and applied to fresh RD cells. This was continued for 10 passages, and was carried out in triplicate for each assay. For the pairwise competition assay, RD cells were inoculated with paired combinations of 7 viruses, giving 21 combinations in total. Each pairwise assay was carried out in a single well and passaged through RD cells 10 times. RNA was isolated from the final supernatants, cDNA was generated and nested PCR carried out to amplify either Region 1 or Region 2 (Primers used are as follows:

Region 1 sense (outer):

(SEQ ID NO 23)
CCCAATTTGATGTAA CACCACACATGG,

Region 1 sense (inner):

(SEQ ID NO 24)
GATATTCCAGGCGAAGTACACAACC,

```
Region 1 antisense (outer):
                                         (SEQ ID NO 25)
CCCATACTCGGATGTGCTTGGG, Region 1 antisense (inner):
                                         (SEQ ID NO 26)
CACTCGGATTGTGCTTGACATCTG, Region 2 sense (outer):
                                         (SEQ ID NO 27)
CAAGGAGCATACACAGGA ATA CC, Region 2 sense (inner):
                                         (SEQ ID NO 28)
GGTACCTACTCTTAGGCAAGCA, Region 2 antisense (outer):
                                         (SEQ ID NO 29)
GAATGTCTGCCTCATCGCCAACT, Region 2 antisense (inner):
                                         (SEQ ID NO 30))
AAGCTGGACGCTTCAATGAGCCT.
```

The amplified fragment was then subjected to selective digest to determine the composition of each virus in the final supernatant. The restriction enzymes used for each competition assay are given in Table 3. Relative band intensity was measured using ImageJ software.

then pelleted and washed again in PBS before RNA was isolated and viral copy number determined by qRT-PCR. Copy number was normalised against the housekeeping gene GAPDH (qRT-PCR primers: Sense GAAATCCCAT-CACCATCTTCCAGG (SEQ ID NO 31); Antisense GAGCCCCAGCCTTCTCCATG (SEQ ID NO 32)).

R1 Transfection—Creating the Transcripts

RNA transcripts were made from Region 1 of the E7 WT and mutant viruses by linearising the original cloning plasmid containing the synthetic insert with HpaI, and carrying out a T7 transcription reaction. The integrity of the 1.3 kb RNA transcripts was confirmed using an Agilent Bioanalyser. A549 cells in 24-plates were transfected with 250 µl RNA using 1.5 µl Lipofectamine 2000 (Invitrogen) per well, and cellular RNA was harvested 6 hours later. Poly 1:C (5 pg/well) was transfected as a positive control. Induction of I FNp was analysed by qRT-PCR (Primers: Sense GAC-CAACAAGTGTCTCCTCCAAA (SEQ I D NO 33); antisense G AACTG CTGCAGCTG CTTAATC (SEQ ID NO 34)) using cycling conditions of 95° C. for 10 mins, followed by 40 cycles of 95° C. for 15 s and 60° C. for 60 s. Copy number was normalised against GAPDH

TABLE 3

Enzymes used in selective digests for competition assays

| Virus 1 | Virus 2 | Region amplified | Enzyme | Restriction site |
|---|---|---|---|---|
| Individual competetion experiments | | | | |
| WT | R1/R2 Permuted | 2 | HindIII | In R1/R2 Permuted |
| WT | R1/R2 CpG-high | 1 | BamHI | In R1/R2 CpG-high |
| WT | R1/R2 UpA-high | 2 | ScaI | In R1/R2 UpA-high |
| WT | R1/R2 CpG-low | 2 | SphI | In R1/R2 CpG-low |
| WT | R1/R2 UpA-low | 2 | EcoRV | In WT |
| Pairwise competition experiments | | | | |
| WT | R1/R2 Permuted | 2 | HindIII | In R1/R2 Permuted |
| WT | R1 CpG/UpA-low | 1 | EcoRV | In WT |
| WT | R2 CpG/UpA-low | 2 | EcoRV | In WT |
| WT | R1/R2 CpG-low | 2 | EcoRV | In R1/R2 CpG-low |
| WT | R1/R2 UpA-low | 2 | EcoRV | In WT |
| WT | R1/R2 CpG/UpA-low | 2 | SphI | In WT |
| R1/R2 Permuted | R1 CpG/UpA-low | 1 | SphI | In R1/R2 Permuted |
| R1/R2 Permuted | R2 CpG/UpA-low | 2 | HindIII | In R1/R2 Permuted |
| R1/R2 Permuted | R1/R2 CpG-low | 2 | HindIII | In R1/R2 Permuted |
| R1/R2 Permuted | R1/R2 UpA-low | 2 | HindIII | In R1/R2 Permuted |
| R1/R2 Permuted | R1/R2 CpG/UpA-low | 2 | HindIII | In R1/R2 Permuted |
| R1 CpG/UpA-low | R2 CpG/UpA-low | 1 | EcoRV | R2 CpG/UpA-low |
| R1 CpG/UpA-low | R1/R2 CpG-low | 2 | SphI | In R1/R2 CpG-low |
| R1 CpG/UpA-low | R1/R2 UpA-low | 2 | EcoRV | In R1 CpG/UpA-low |
| R1 CpG/UpA-low | R1/R2 CpG/UpA-low | 2 | EcoRV | In R1 CpG/UpA-low |
| R2 CpG/UpA-low | R1/R2 CpG-low | 2 | EcoRV | In R1/R2 CpG-low |
| R2 CpG/UpA-low | R1/R2 UpA-low | 2 | SphI | In R2 CpG/UpA-low |
| R2 CpG/UpA-low | R1/R2 CpG/UpA-low | 1 | EcoRV | In R2 CpG/UpA-low |
| R1/R2 CpG-low | R1/R2 UpA-low | 2 | EcoRV | In R1/R2 CpG-low |
| R1/R2 CpG-low | R1/R2 CpG/UpA-low | 2 | EcoRV | In R1/R2 CpG-low |
| R1/R2 UpA-low | R1/R2 CpG/UpA-low | 2 | SphI | In R1/R2 CpG/UpA-low |

Early Intra-Cellular Replication Kinetics

To induce synchronous infection, RD cells in 24-well plates were cold-treated at 4° C. for 5 minutes before inoculation with wild type or mutant virus normalised for genome copy number. A total of 2×10$^8$ genome copies (1000 per cell) were applied to each well, and the cells were maintained at 4° C. for a further 30 minutes before being moved to 37° C. Cells were washed twice with PBS and then trypsinised 1 hour or 4 hours post infection. The cells were Results Strategy for Maximising or Minimising CpG/UpA Content in Mutant Viruses Like other small RNA viruses, the frequency of CpG dinucleotides in the E7 genome was suppressed relative to the expected frequency based on its G+C content, with an observed to expected ratio of CpG dinucleotides in the coding sequence of E7 of 0.58. Frequencies of UpA dinucleotides were also suppressed in the E7 genome (observed to expected ratio of 0.78).

To investigate whether CpG and UpA dinucleotide frequencies influenced the ability of E7 to replicate in vitro, we created a series of mutated viruses in which frequencies of both nucleotides were changed from their native levels. This was achieved using the reverse genetics system developed for enteroviruses, in the current study with the pT7:E7 infectious clone. RNA transcripts generated from a linearised plasmid containing the E7 complete genome sequence generate infectious virus for phenotypic characterisation after transfection into a wide range of mammalian cells.

To select sequences for mutagenesis, we sought to avoid regions of the genome that contained RNA elements required for replication or translation functions of the virus, such as the cis-replicating element embedded in the 2C coding sequence (Goodfellow et al. 2000, Journal of Virology 74: 4590-4600).

Although incompletely located and functionally characterised to date, the presence of required non-coding elements can be revealed through analysis of RNA secondary structure formation in these regions and through suppression of synonymous sequence variability that reflects non-coding functional constraints on sequence change in these regions (FIG. 8). By scanning an alignment of complete genome sequences of each of the current described species B serotypes (including the pT7:E7 sequence of the infectious clone), an area of marked suppression of sequence variability co-localised in the 2C region with the CRE. Calculation of folding energies to detected RNA secondary structure in the genome showed prominent regions of structure in the 5'UTR, 3'UTR and the CRE. The remainder of the genome showed no evidence for consistent RNA structure formation (MFED values around zero).

Figure 5:
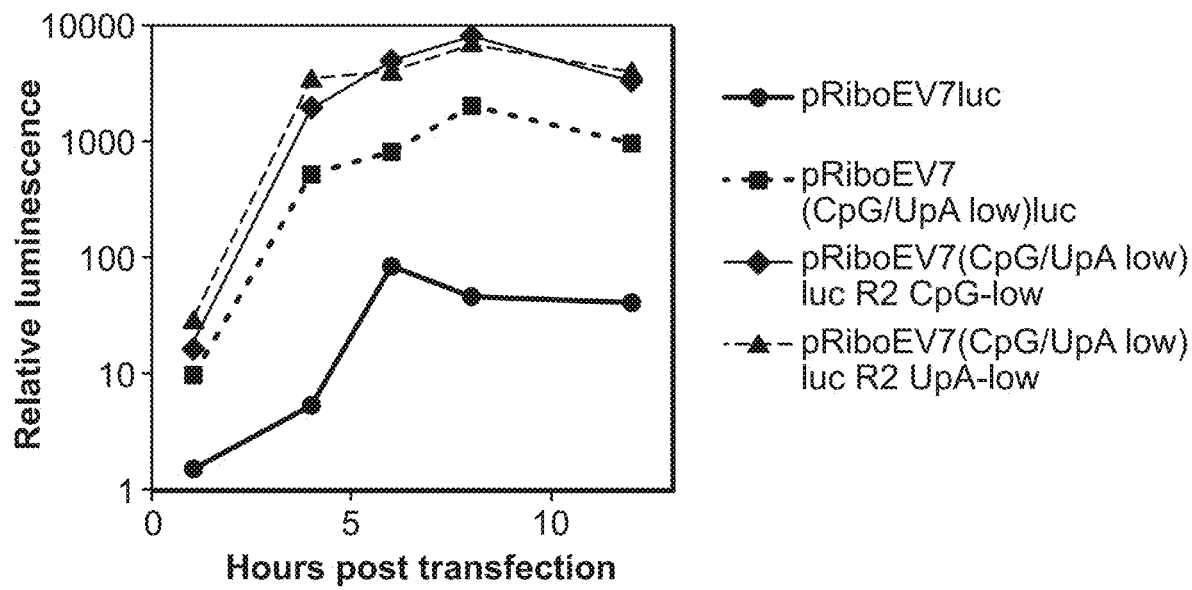
FIG. 5. Analysis of luciferase expression driven by E7 replicons with reduced CpG/UpA frequencies. Replicons were generated with reduced CpG/UpA frequencies, based on the backbone pRiboE7luc replicon, in which the structural genes of E7 are replaced by an insect luciferase gene. In the pRiboE7(CpG/UpA low)luc replicon the luciferase gene itself was modified to minimise both CpG and UpA frequency; in the pRiboE7(CpG/UpA low)luc R2 CpG-low and pRiboE7(CpG/UpA low)luc R2 UpA-low replicons Region 2 was additionally modified to further reduce either CpG or UpA frequency. RNA was generated from replicons and 50 ng transfected into RD cells.

The combination of unrestricted synonymous variability and an absence of RNA secondary structure over long stretches of the E7 genome provided opportunities for altering dinucleotide frequencies without impairing virus replication for other reasons. Two genome regions (at positions 1878-31 19 and 5403-6462) were selected for mutagenesis based on these criteria. Sequences were modified by replacing nucleotides within CpG or UpA dinucleotides with alternative bases that preserved coding. It was possible to remove all CpG dinucleotides from both regions and reduce UpA to frequencies approximately one third of wild type levels (Table 1; CpG-low and UpA-low insert sequences). As an alternative strategy to maximise frequencies of these dinucleotides, every site that could tolerate the creation of these dinucleotides without changing coding was identified and mutated to create sequences with 2.5×3× the their naturally occurring frequencies (Table 1 ; CpG-high, UpA-high). To ensure that sequence disruption did not damage or destroy undetected replication element within Region 1 and 2, sequences from these regions were permuted using the algorithm CDLR in the SSE sequence package (E7-permuted in Table 1). This randomises the order of codons within the sequence while maintaining coding and dinucleotide frequencies through swaps between equivalently coding triplets in the same upstream and downstream dinucleotide contexts. All insert sequences were then synthesised and cloned into the pT7: E7 infectious clone using naturally occurring restriction sites. Clones were creating with one or both regions replaced by modified insert sequences.

Replicative Fitness of Mutants with Modified CpG/UpA Frequencies

Wild type E7 and mutant viruses were recovered in tissue culture by transfecting whole-genome RNA sequences obtained through T7 transcription of pT7: E7. Recovered virus was then titred by TCID50 and used in subsequent experiments.

Particle to infectivity ratio. RNA copy to infectivity ratios were determined by extracting viral RNA from a known infectious titre of each virus, and carrying out qRT-PCR. The ratios are shown in FIG. 1. The RNA to infectivity ratio of the permuted double region mutant (247±9.2) was similar to that of the WT E7 virus (354±8.0), indicating that the process of synonymous nucleotide replacement itself does not affect RNA to infectivity ratio where dinucleotide frequencies are kept constant. In contrast, increasing the either the CpG or UpA dinucleotide frequency drastically affected RNA to infectivity ratio, with the value for the double region CpG-high mutant being approximately 350 times the WT value (128,840±31698.6) and the UpA-high mutant approximately 20 times higher (6233±883.6). The RNA to infectivity ratio for the double region CpG-low and UpA-low mutants was comparable to the WT.

ii) Replication kinetics with low MOI infection. In a low-MOI multi-step infection the growth kinetics of the E7 mutants was compared to that of the WT. Increasing the CpG or UpA dinucleotide frequency caused a severe attenuation of viral replication, resulting in a viral output 6854-fold lower in the R1/R2 CpG-high than the WT after 24 hours, and a 30-fold lower output in the R1/R2 UpA-high mutant (FIG. 2*a*). Mutant viruses replicated more slowly as well as producing a lower final output of infectious particles. Dose-dependency was demonstrated, as viruses with only one region mutated tended to replicate better than the double region mutants. Increasing dinucleotide frequencies in Region 2 was more detrimental to viral replication than Region 1, despite its shorter length (1 kb compared to 1.3 kb). R1 CpG-high mutants replicated only 144-fold less than wild type at 24 hours, whilst R2 CpG-high mutants replicated 1487-fold less (FIG. 2*c*). Amongst the UpA-high mutants, replication was actually improved by modifying R1, giving a 10-fold higher output than wild type, whilst the R2 mutant fared slightly worse than the double mutant. The replication rate of the R1/R2 permuted control was indistinguishable from wild type. Lowering the CpG and UpA dinucleotide frequency compared to the WT level actually had a positive effect on viral replication, albeit more subtle than for the high mutants (FIG. 2*b, c*). The replication rates and final viral outputs of the CpG-low and UpA-low double mutants were similar to wild type, however the replication of the R1/R2 CpG/UpA-low double mutant was 10-fold higher than the wild type at both 18 and 24 hours post infection.

iii) Plaque morphology. Increasing CpG and UpA frequency also negatively affected plaque area (FIGS. 3*a-b*). The size reduction in CpG-high mutants was dose-dependent, with the R1 mutant plaque area 3.5-fold lower than the E7 WT and the R1/R2 mutant 8.8-fold lower. R1/R2 UpA-high plaques were on average 3.2-fold smaller than the wild type, demonstrating again a less severe phenotype than the equivalent double region CpG-high mutant. The area of R1/R2 UpA-low plaques was comparable to WT, whilst the R1/R2 CpG-low mutant produced significantly larger plaques, 1.4-fold greater than the WT.

iv) Replication kinetics of a sub-genomic replicon. The replication kinetics of CpG- and UpA-low mutants were further characterised using a sub-genomic replicon system expressing a luciferase gene, in order to provide a more sensitive measure of viral genome replication. Bioinformatic analysis of the original pRiboE7luc 1.7 kb firefly luciferase gene revealed a strikingly high observed to expected CpG ratio, of 1.242. This is characteristic of insect genomes, in which CpG frequency is not suppressed (Burge et al. 1992, Proceedings of the National Academy of Sciences of the United States of America 89: 1358-1362). Despite the widespread use of such reporter systems, the results obtained in the current study and those of Burns et al. (2009) suggested that the high CpG ratio could drastically impede the replication rate of this viral replicon in mammalian cell lines. A replacement luciferase gene was therefore designed in which the CpG ratio was reduced to 0.013 and the UpA ratio to 0.145 (from 0.699) through synonymous substitution, as described previously. Following this, Region 2 of the resulting modified replicon was replaced with the CpG-low or UpA-low inserts used in generating the original double region mutants. Fluorescence was then analysed over a 12-hour time-course following transfection of each replicon (FIG. 5). A dramatic increase in replicative ability was conferred by the replacement of the original insect luciferase gene with the synthetic CpG/UpA low gene, giving a 100-fold difference in relative luminescence at 4 hours. Replication rate was heightened further by the addition of the Region 2 CpG- or UpA-low inserts, to a maximum of 6-fold after 6 (CpG-low) or 4 (UpA-low) hours relative to the pRiboE7luc CpG/UpA low replicon. The results demonstrate that by reducing CpG or UpA frequencies to below wild type levels, replicative fitness of E7 can actually be improved in a cell culture environment. Furthermore, the efficiency of transgenic reporter genes may be improved by at least 100-fold by optimising CpG and UpA frequencies according to the genetic system under study.

Investigation of Virus Particle Integrity

Figure 1:
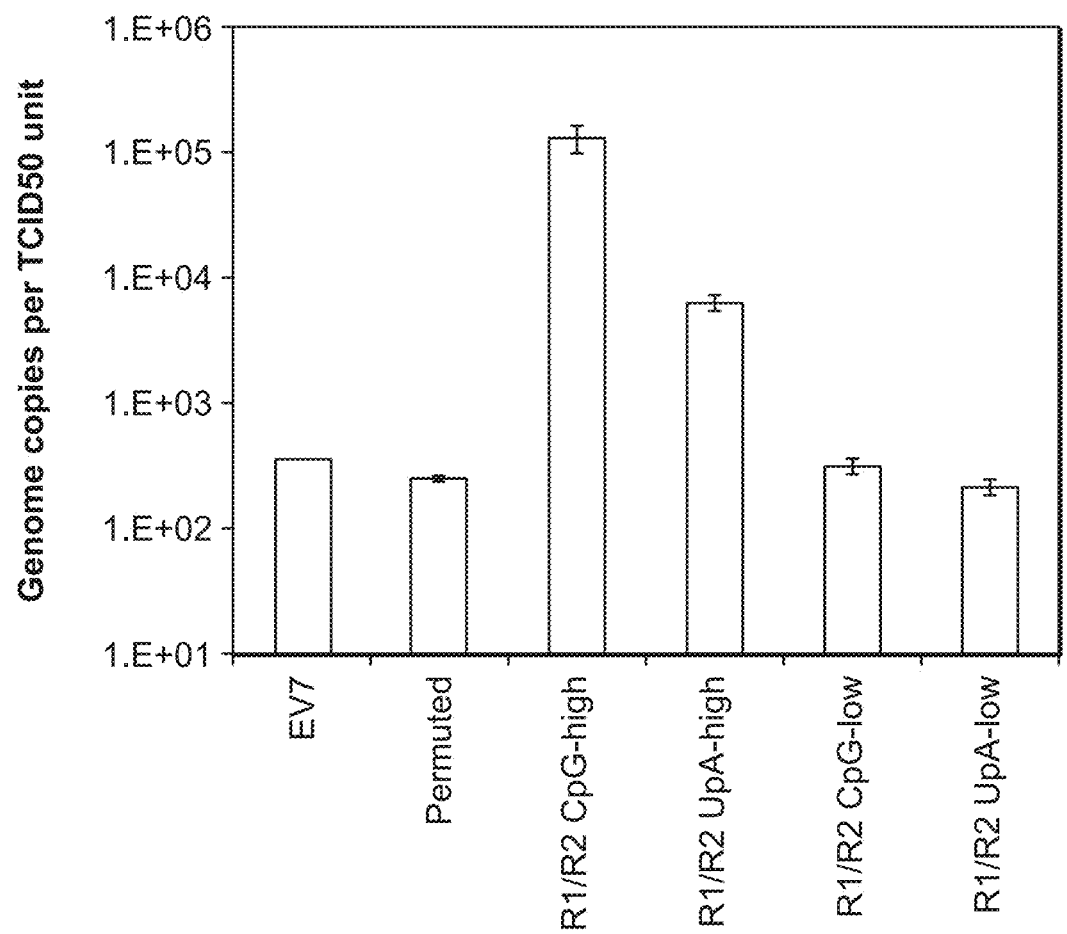
FIG. 1. RNA to infectivity ratios of WT and viruses with modified CpG/UpA frequencies. WT and mutant viruses were recovered from RD cells and titred by TCID50. The number of viral genome copies was determined through qRT-PCR and compared with the infectivity titre. Results are the mean and standard error from three separate extractions.
Figure 2A:
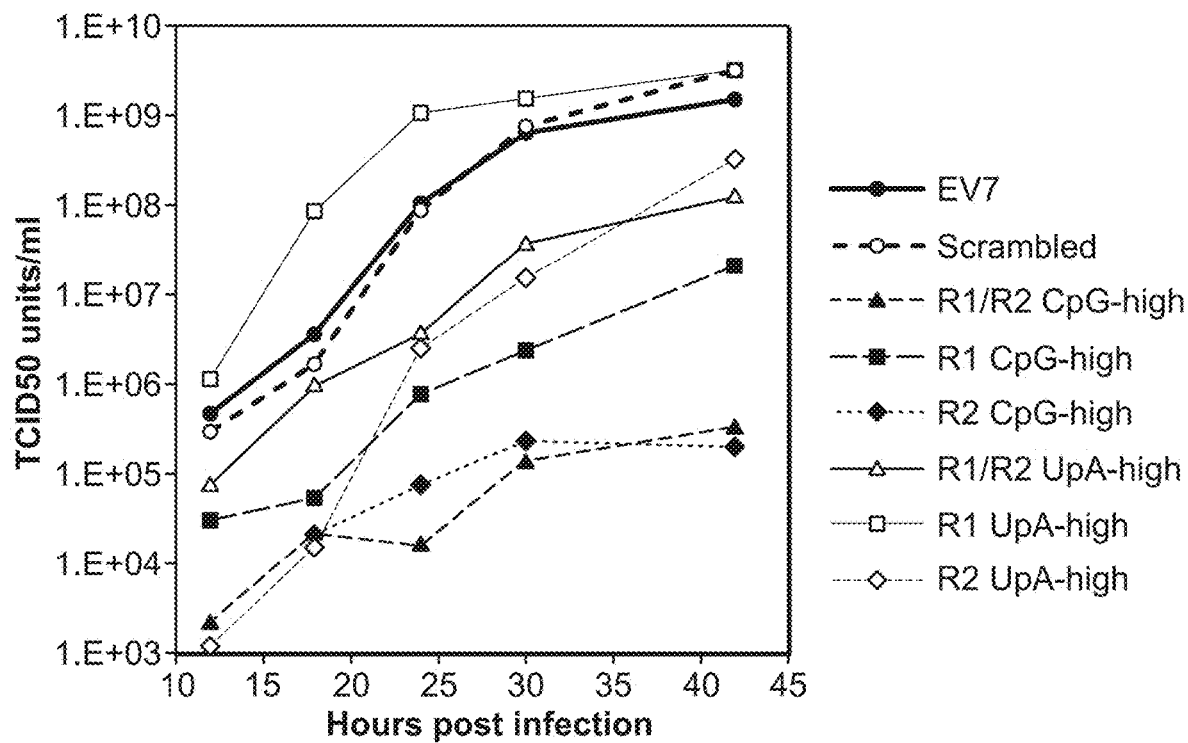
FIG. 2A-C. Replication kinetics of WT and modified viruses infected at a low MOI. RD cells were infected with E7 WT, permuted, CpG/UpA-high mutant (A) and CpG/UpA-low mutant (B) virus at an MOI of 0.01. The inoculum was removed and cells washed after 1 hour. The infectious titre of cell supernatants was then analysed at a range of time points by TCI D50. Results are the mean of three biological replicates. The mean titre and standard error of all the viruses is shown at 24 hours post infection (C).
Figure 2B:
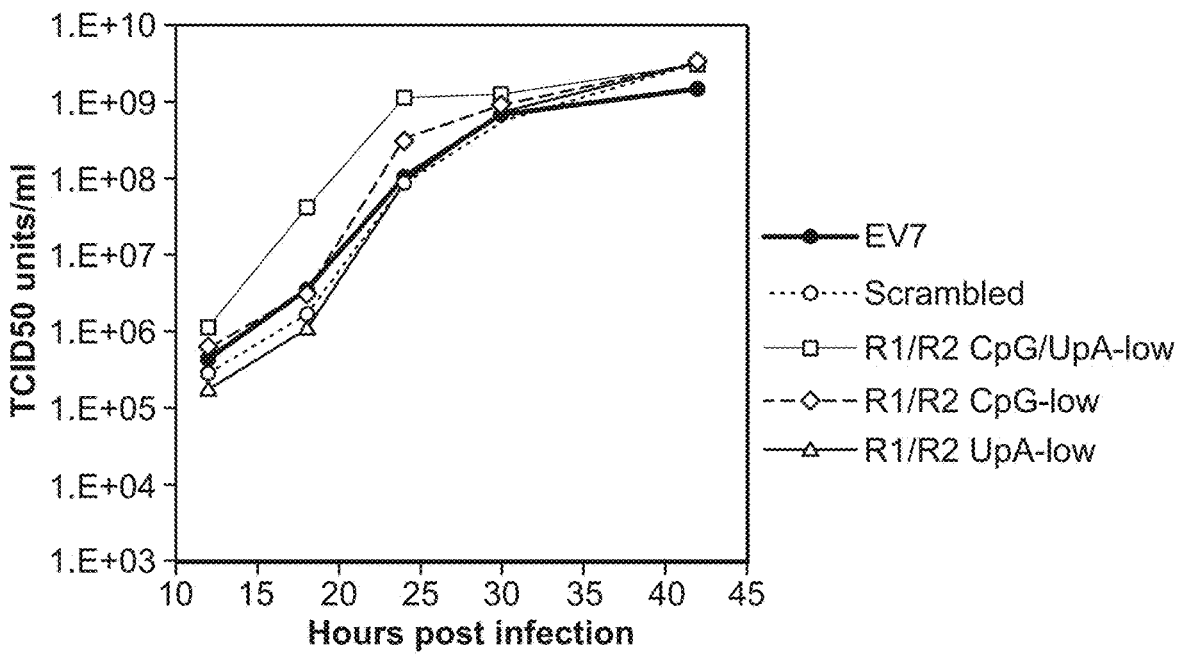
Figure 2C:
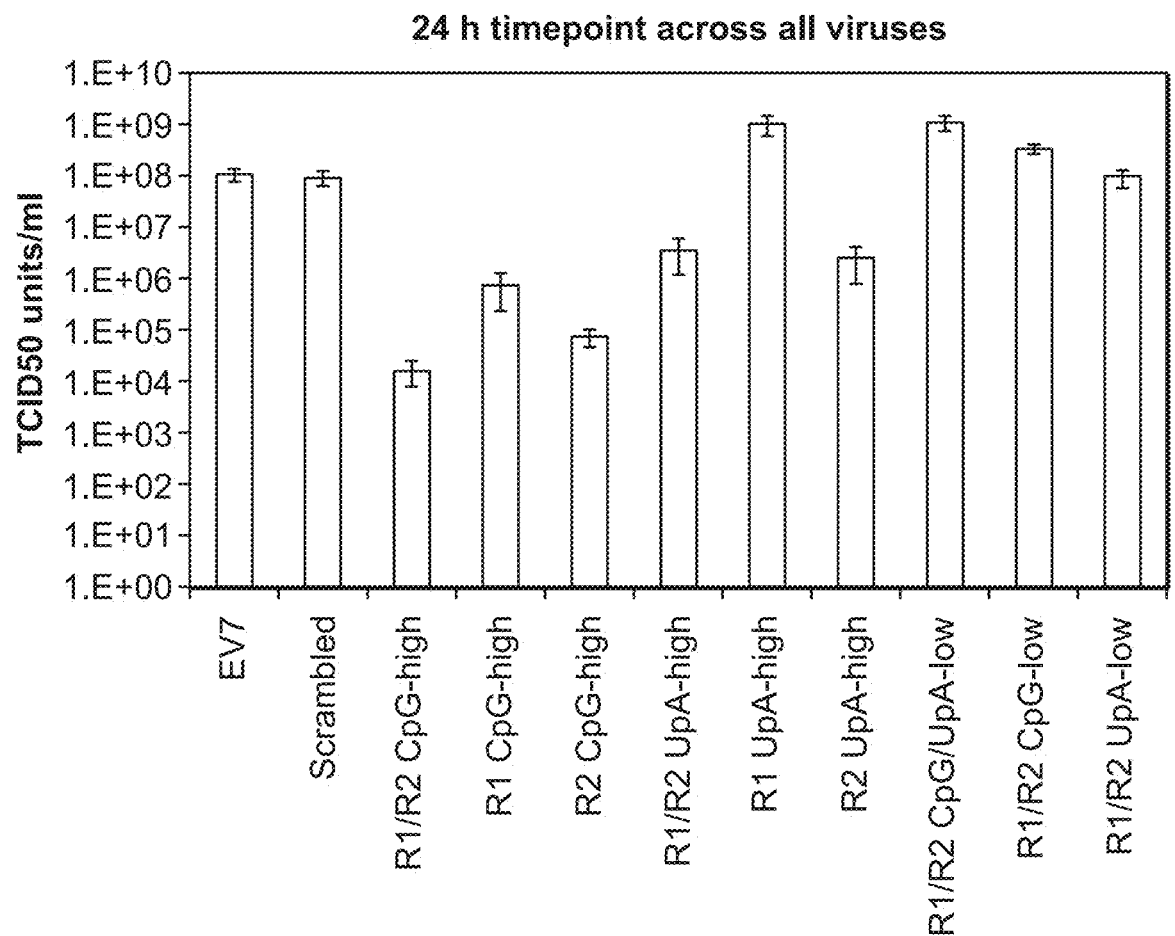
Figure 3A:
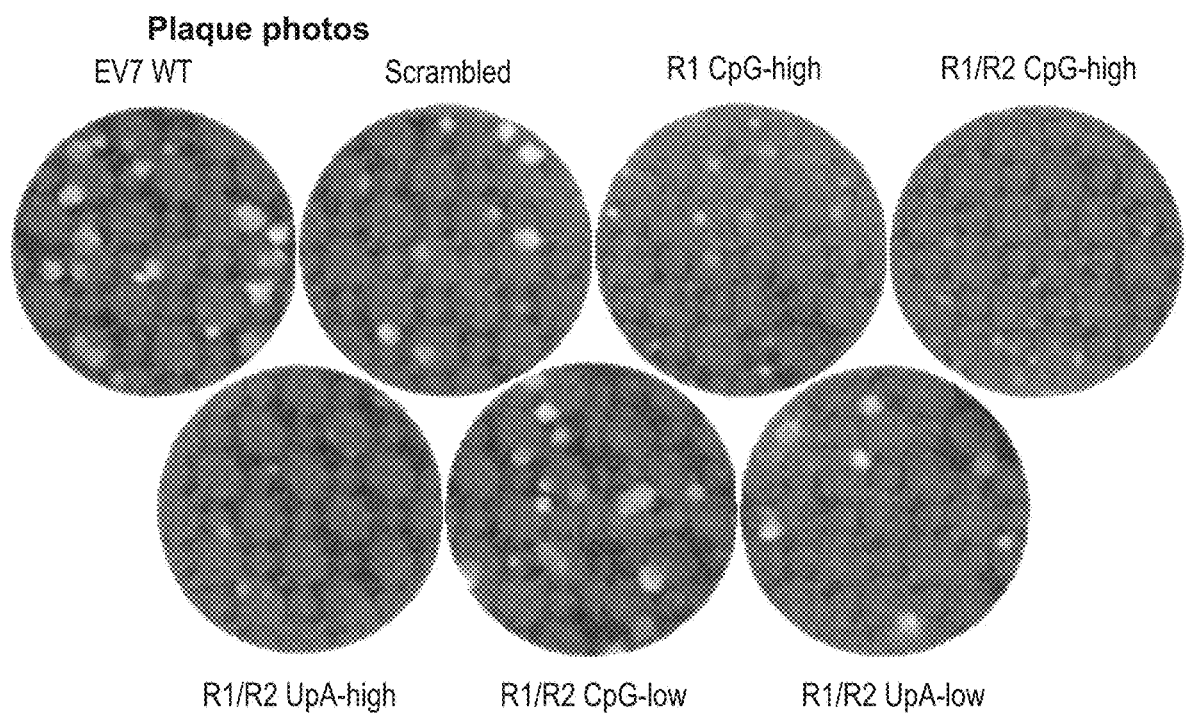
FIG. 3A-B. Plaque morphology of E7 WT and modified viruses. RD cell monolayers in 10 cm plates were infected with a similar infectious titre of virus and incubated for 96 hours at 37° C. (A). Plaque area was determined using ImageJ software (B). Results are the mean of an equal number of plaques selected randomly from one plate per virus. Asterisks show a significant difference from the WT value as determined by t test (*$p<0.05$, **$p<0.01$).
Figure 3B:
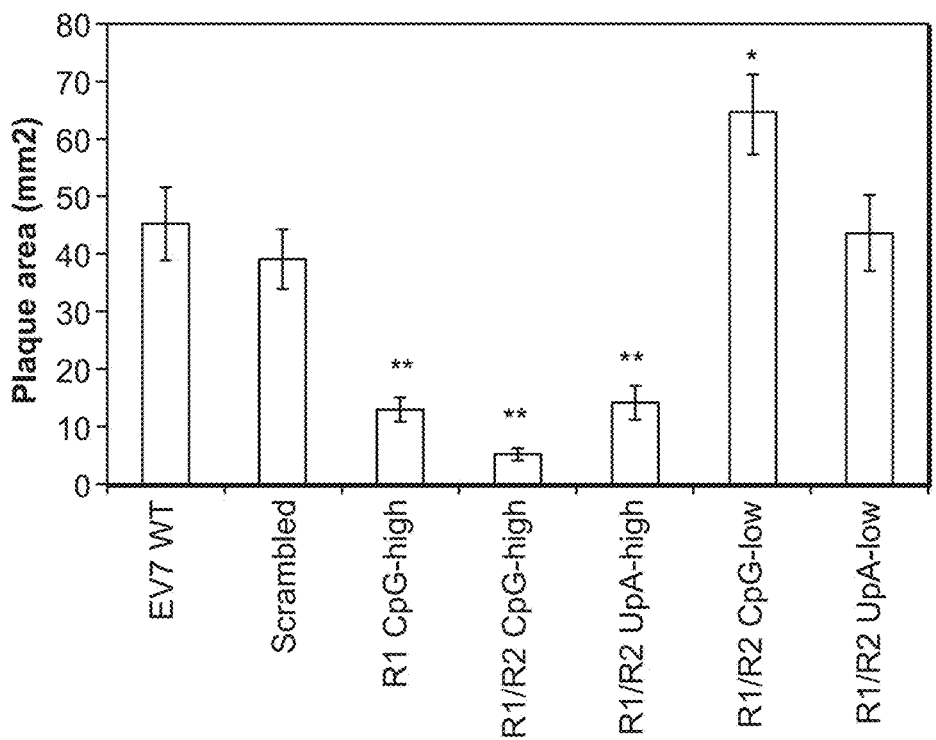
Figure 4:
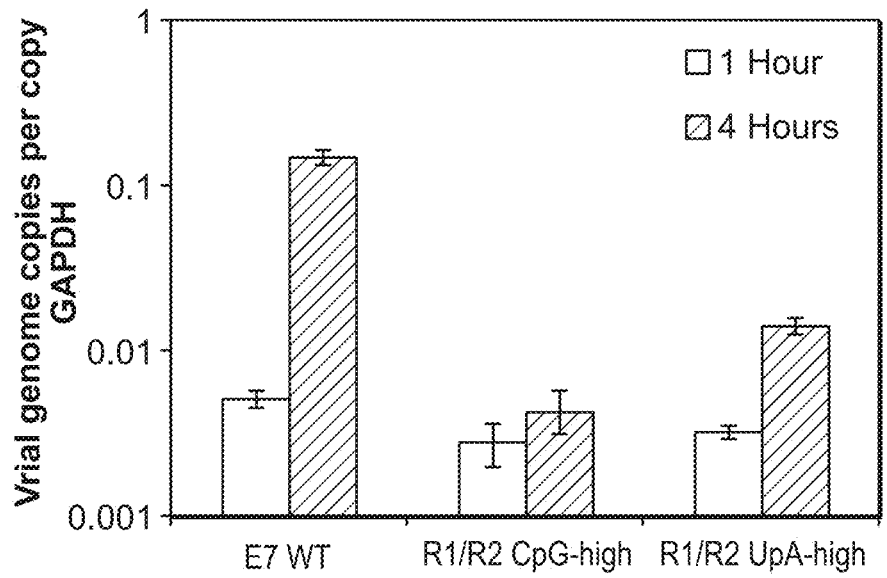
FIG. 4. Synchronised infection with equal viral genome copies. Cells were synchronously infected with 1000 genome copies of WT, R1/R2 CpG-high or R1/R2 UpA-high virus, as calculated using qRT-PCR. Cells were trypsinised and washed 1 or 4 hours post infection and the intracellular viral load determined by qRT-PCR. Results are the mean and standard error of three biological replicates.

In order to determine whether the impaired replication rate observed in CpG and UpA-high mutants was due to a reduction in the ability of virus particles to enter cells, a comparison was made between the number of virus particles used to infect cells and the number of intracellular vial genome copies present immediately post infection. One hour after a synchronous infection with 1000 virus particles per cell (as determined by qRT-PCR), the number of intracellular viral genome copies was found to be similar between viruses, with 42 per cell in wild type E7, 19 per cell in R1/R2 CpG-high, and 36 per cell in R1/R2 UpA-high, see FIG. 4. Four hours post infection, after initiation of viral genome replication, a clear differentiation was observed between viruses. The number of wild type genome copies had increased to 2362 per cell, whilst CpG-high copies remained at 58 per cell and UpA-high at 207 per cell. Increasing CpG or UpA dinucleotide frequencies therefore affects viral genome replication at an early stage post infection.

Fitness Comparison of Modified Viruses using Competition Assays

The relative fitness of high and low mutant viruses compared to E7 WT was confirmed using competition assays. Following infection with an equal MOI of each virus and serial passage in tissue culture, R1/R2 CpG-high and R1/R2 UpA-high each became rapidly out-competed by the WT, being un-detectable by PCR after 5 passages (FIG. 6). Further analysis of CpG-high mutants showed that the R1/R2 mutant was already being out-competed after 1 passage, whereas the R1 and R2 mutants were out-competed more slowly due to their higher relative fitness. Similarly, the individual R1 and R2 UpA-high mutants were still abundant after 5 passages.

Confirming the replicative advantage revealed by the CpG-low and UpA-low replicons, the R1/R2 CpG- and UpA-low mutants demonstrated a higher relative fitness than WT, out-competing it completely after 15 passages, and showing at least 90% prevalence after only 10 passages (FIG. 6). To investigate this phenomenon further, a pairwise competition experiment was carried out whereby combinations of single or double region CpG- and/or UpA-low mutants were competed against one another, allowing a fitness ranking to be determined (FIG. 7a-b). The R1/R2 CpG/UpA-low mutant had the highest fitness, completely out-competing almost all of the other viruses by passage 6. The double region CpG-low ranked second, followed by the single region R1 CpG/UpA-low mutant. Lowering CpG/UpA frequency in Region 1 was demonstrated to have more effect than in R2, as the R2 mutant was rapidly out-competed by R1 CpG/UpA-low as well as the double region UpA-low mutant, an effect that might be expected due to the relative sizes of the modified fragments (Region 1 is 1.3 kb whereas R2 is 1 kb). The reduction of CpG frequency was shown to have a greater effect than that of UpA, whereas increasing the CpG level was more detrimental to viral replication than UpA.

Effect of Dinucleotide Frequency Changes in other RNA Viruses

To investigate the generality of the replication enhancement observed in E7 in other virus systems, the inventor constructed mutants of the murine Theiler's virus (TMEV), a picornavirus in the genus Cardiovirus and of influenza A virus (IAV) with regions of the genome replaced with modified coding sequences. These were similarly designed to contain elevated or lowered CpG and UpA dinucleotide frequencies while retaining protein and avoiding areas of the genome containing known or suspected RNA secondary structures or packaging elements (IAV).

Replication competent mutant of TMEV was constructed with a region of the genome between positions 5445-6702 replaced with modified sequences (numbering based on the TMEV GD7 clone [accession number X56019]). Mutants with elevated frequencies of CpG and UpA showed substantial impairment of virus replication (FIG. 9) while the CpG/UpA-low mutant showed enhanced replication compared to wild type (WT) virus. CpG- and UpA-high mutants showed elevated RNA/infectivity ratios compared to WT. The degree of replication enhancement/attenuation observed in TMEV was similar in extent to those of E7 mutants with comparable degrees of genome replacement (single region mutants).

Several mutants of IAV have been constructed in which one or more genome segments were replaced with modified insert sequences. As an example of the results obtained, mutants with a segment with increased CpG or UpA showed attenuated replication and an increased RNA/infectivity ratio. These changes in phenotype were comparable in magnitude to those observed in E7 (and TM EV). The replication cycle of IAV is substantially different from those of E7 and TMEV and indicates that the restrictions imposed by possession of CpG and UpA dinucleotides on replication/gene expression likely represent fundamental aspects of RNA virus replication. Dinucleotide frequencies therefore may influence replication rates of a much wider range of mammalian, avian and plant viruses that show similar suppression of CpG and UpA dinucleotide frequencies.

Influence of Dinucleotide Frequencies on Reporter Gene Expression.

A variety of genes are used as reporters or selectable markers in biotechnology, as components of expression vectors, transgenes and replicons. Reporter genes or selectable markers are frequently derived from prokaryotes (e.g. antibiotic resistance genes) or lower eukaryotes (e.g. luciferase, green fluorescent protein). Most derive from organisms without reduced or absent host genome DNA methylation and consequently lack the suppression of CpG dinucleotides observed in vertebrate sequences and in RNA viruses infecting them. The inventor hypothesised that high CpG frequencies in commonly used reporter genes such as firefly luciferase (derived from the insect Photinus pyralis) may have a generic, harmful effect on gene expression and replicative ability of replicons containing them. The inventor has previously observed substantial enhancement in luciferase expression and replication of the E7 replicon though insertion of a zero-CpG, low UpA replacement luciferase sequence. The inventor has now observed the same phenomenon in the HCV replicon.

The Con1 replicon is widely used to study the replication of hepatitis C virus (Lohmann et al. 1999, Science 285: 110-1 13). A currently widely used Con1-derived construct (Krieger et al. 2001, J. Virol. 75:4614-4624) contains a luciferase reporter gene similar to that used in the E7 replicon and which shows similarly elevated CpG frequencies. The inventor replaced this with a CpG-zero, UpA-low synthetic sequence and compared luciferase expression with the parental sequence.

This degree of replication enhancement of the HCV replicon exceeded that even of E7. Remarkably, in its unmodified form, the Con1 HCV replicon has been used in replication assays in academic research and by the pharmaceutical industry for antiviral development for over 12-13 years without any idea that its replication is fundamentally compromised by inserted reporter genes (see FIG. 10). This underlines the novelty of the discovery described in the instant disclosure.

Similar modifications can be made to a red fluorescent protein (RFP) expressing HCV replicon construct. In this specific case, commonly used RFP sequences as transgenes and other vectors show CpG frequencies of over 0.6 (observed to expected ratio) which potentially also influence their expression and mediate unintended cellular activation processes.

Not only does luciferase (and likely other high CpG reporter genes) reduce the replication of replicons (e.g. E7 and HCV) but their intracellular expression has a likely substantial effect on the non-physiological activation of cellular defence pathways (Atkinson et al. 2014, Nucleic acids research, gku075). These have potentially compromised studies of effects of innate immune responses to viral replication in cells. Similar concerns about potential toxicity and cellular activation effects naturally arise when considering the use of these and other sequences with high CpG frequencies as selection or reporter genes in wider areas of biotechnology. The instability of many sequences used as transgenes may originate through recruitment of innate and inflammatory responses against cells expressing such reporter genes or selection markers.

CpG and UpA Removal to Enhance Virus Replication in the Manufacture of Inactivated Virus Vaccines.

By quantitative PCR and infectivity assays, accelerated replication of CpG/UpA-low mutants in multistep replication assays has been demonstrated, but to reinforce this it is useful to show further that enhanced replication produces greater yields of viral proteins that represent the protective component of a vaccine.

The inventor infected RD cells with wild type echovirus 7 and the CpG/UpA-low mutant. Cells were harvested at several time points after infection and expression of viral capsid protein extracted from cells and supernatant quantified by Western blot using a specific anti-capsid monoclonal antibody (FIG. 11).

The CpG/UpA-low echovirus 7 mutant showed enhanced capsid protein expression throughout the time course of the experiment, quantified at levels of 2-fold higher than the WT control at 12 hours and increasing to 14.5-fold at 18 hours Translated to a poliovirus system, this provides the evidence required for the ability of this mutational process to substantially improve inactivated virus vaccine production yields.

The experimental results depicted in FIG. 11 were obtained from a mutant E7 with approximately 30% of the genome replaced by CpG/UpA-low mutated sequences. Further enhancement of virus replication and viral protein production can almost certainly be achieved through further replacement of sequences in other parts of the coding region of the genome. In E7 and likely in poliovirus, one is typically able to replace up to 80% of the genome with CpG/UpA-low sequences and achieve further enhancement of virus replication. For influenza A virus it is expected that segments 1, 4, 5 and 6 (collectively approximately 43% of the genome) can be replaced with CpG/UpA-low sequences. Segments 4 and 6 encode the haemagglutinin and neuraminidase proteins that represent the principal protective components in the inactivated IAV vaccine.

DISCUSSION

High Mutants

The first part of this study demonstrated that specifically increasing the frequency of CpG or UpA dinucleotides in E7 results in severe viral attenuation. Attenuation was characterised by a dramatic reduction in replication rate, smaller plaque area, low particle to infectivity ratio and a low competitive fitness relative to WT E7. The results agree with the outcome of previous studies in poliovirus, in which codon replacement or de-optimisation leading to an increase in CpG/UpA frequency correlated negatively with replicative fitness (Burns et al. 2009, J. Virol. 83:9957-9969, Coleman et al. 2008, Science. 320:1784-1787). A reduced RNA to infectivity ratio due to higher CpG and UpA frequencies was also observed in poliovirus (Burns et al. 2009, J. Virol. 83:9957-9969). Increasing CpG and UpA in E7 had a greater effect than in poliovirus, where introducing 105 new CpG dinucleotides in the capsid region led to approximately a 3-fold reduction in infectivity output (Burns et al. 2009, J. Virol. 83:9957-9969). In E7, introducing 129 new CpGs in the capsid region led to a 74-fold reduction in infectivity titre, whilst introducing 116 CpGs into the region of non-structural genes caused a 7500-fold reduction. Similar experiments are currently underway using Theiler's murine encephalomyelitis virus (TMEV) and influenza A virus, in which increased CpG or UpA frequency also results in a decrease in viral replication (data not shown). Our results show definitively that experimental attenuation of viral fitness is specifically related to CpG and UpA frequencies and is irrespective of %G+C content, also dispelling theories that fitness is determined by non-preferred codon replacement itself or by codon pair bias (Coleman et al. 2008, Science. 320: 1784-1787, Burns et al. 2009, J. Virol. 83:9957-9969). The permuted control used in this study negates the possibility that attenuation is due to disruption in RNA secondary structure. Furthermore, replication defects are unlikely to result from a decrease in translational efficiency, as previous studies have shown that protein synthesis levels are unaltered even for highly attenuated viruses (Burns et al. 2006, J. Virol. 80:3259-3272, Burns et al. 2009, J. Virol. 83:9957-9969).

Changes in CpG frequency had a greater effect on viral replication than changes in UpA levels, being both more beneficial to replication when lowered, and more detrimental when raised. When competed directly, the double region CpG-low mutant showed clear selective advantage over its counterpart UpA-low mutant. This could be attributed to the differences between final CpG and UpA frequency in the modified regions; CpGs were eliminated to a greater extent than UpAs in the low mutant, whilst more were introduced in the high mutant. However, this seems unlikely to account for the difference in fitness. In poliovirus, CpG-high mutants also exhibited a more severe attenuation than UpA-high mutants (Burns et al. 2009, J. Virol. 83:9957-9969), and selection against CpG dinucleotides has been shown to be greater than against UpA during serial passage of codon-deoptimised virus (Burns et al. 2006, J. Virol. 80:3259-3272). The dissimilar patterns of CpG and UpA suppression amongst organisms points to different selective pressures acting upon each dinucleotide (Burns et al. 2009, J. Virol. 83:9957-9969). CpG frequency is widely suppressed in higher eukaryotes and the small viruses that infect them (Karlin et al. 1994, J Virol 68, 2889-2897, Burge et al. 1992, Proceedings of the National Academy of Sciences of the United States of America 89: 1358-1362), whilst UpA suppression is almost universal. UpA-rich RNA is degraded in mammalian host cells by the antiviral endonuclease RNase L, which cleaves UpU or UpA dinucleotides in ssRNA (Washenberger et al. 2007, Virus Res 130, 85-95., Duan and Antezana. 2003, J Mol Evol 57, 694-701). Not being subject to methylation, small RNA viruses may have evolved to mimic both the CpG and UpA dinucleotide composition of their hosts, but for different evolutionary reasons (Burns et al. 2009, J. Virol. 83:9957-9969). The difference between CpG-suppressed mammalian genomes and non-suppressed lower eukaryote genomes may account for the results observed by Nougairede and colleagues (Nougairede et al. 2013, PLoS Pathog 9, e1003172), who found that viruses with de-optimised codons had a higher relative fitness in insect cells compared to mammalian cells. These data support the hypothesis that higher eukaryotes can identify non-self RNA by detecting higher CpG and UpA frequencies than are present in their own RNA.

Low Mutants

Surprisingly, viral replication was enhanced by designing mutants with lower CpG and UpA frequencies than WT. Mutants in which CpGs were eliminated entirely from two modified regions (representing 30% of the genome) outcompeted WT in serial passage, whilst a replicon with CpGs removed from only 14% of the genome showed a 6-fold higher replication rate than the WT. Similar results were obtained for UpA-low mutants, despite the fact that UpAs could not be completely eliminated from the modified regions. Mutants in which both CpG and UpA frequency was minimised in both regions showed an even higher level of replicative fitness. These unprecedented findings, confirmed by several different assays, reveal an entirely novel phenomenon that would not have been predicted based on the results obtained from the CpG- and UpA-high mutants. If the host mechanism for detecting CpG and UpA in foreign RNA is based on sensing dinucleotide frequencies higher than in its own RNA, there is no immediate reason why viruses with non-physiologically lowered frequencies should do better than those with frequencies identical to the host. One explanation is that the system for recognising and limiting replication of RNA with high CpG/UpA is optimised at a sensitivity level that prioritises avoiding false negatives. Due to the importance not letting viral RNA go un-detected, occasionally RNA with a WT level of CpG/UpA could be targeted. In this situation, RNA with low CpG/UpA would have an advantage. Whether the CpG/UpA-low mutants could maintain their replicative advantage in a whole organism system is unclear. The heightened replication rates observed in viruses with reduced CpG/UpA ratios could provide opportunities for vaccine production. Where the vaccine involved a killed virus, an improved replication rate in cell culture would allow a higher production rate of a virus with identical antigenicity to the original.

The various molecular biological and other associated techniques to perform the present invention are well known to the skilled person, and there is a plethora of reference material available on the subject which would form part of their common general knowledge. While specific techniques have been described in detail above, it is perfectly within the ability of the skilled person to modify or adapt the techniques described above to work within the scope of the present invention. A suitable reference text in respect of the various techniques discussed in the present application is Green & Sambrook, Molecular Cloning: A Laboratory Manual (Fourth Edition), 2012, Cold Spring Harbor Laboratory Press.

The invention claimed is:

1. A method of producing a synthetic RNA expression vector, the method comprising:
   modifying at least one region of a primary nucleotide sequence which reduces the frequency of at least one of CpG and UpA dinucleotides in said at least one region, thereby producing a modified primary nucleotide sequence; and
   producing a synthetic RNA expression vector comprising said modified primary nucleotide sequence which has a reduced frequency of at least one of CpG and UpA dinucleotides compared to a synthetic RNA expression vector which comprises an unmodified primary nucleotide sequence.

2. The method of claim 1 which comprises a step of preparing a DNA polynucleotide which encodes a synthetic polynucleotide having a reduced CpG and/or UpA frequency.

3. The method of claim 2 which comprises a step of transcribing said DNA polynucleotide to form a synthetic RNA polynucleotide having a reduced CpG and/or UpA frequency.

4. The method of claim 1, wherein the synthetic RNA expression vector is a recombinant RNA viral vector.

5. The method of claim 4, wherein the synthetic RNA expression vector is a recombinant virus genome, optionally wherein the synthetic RNA expression vector is a recombinant single stranded RNA (ssRNA) virus genome.

6. The method of claim 5, wherein the at least one region of said primary nucleotide sequence which is modified to reduce the frequency of at least one of CpG and UpA dinucleotides is the entire recombinant virus genome.

7. The method of claim 1, wherein the frequency of both CpG and UpA dinucleotides is reduced in the synthetic RNA expression vector comprising said modified sequence, as compared to the synthetic RNA expression vector which comprises an unmodified primary nucleotide sequence.

8. The method of claim 1, wherein the at least one region of said primary nucleotide sequence which is modified to reduce the frequency of at least one of CpG and UpA dinucleotides is of at least 30 nucleotides in length, optionally the at least one region is of at least 100 nucleotides in length, optionally the at least one region is of at least 200 nucleotides in length, optionally the at least one region is of at least 500 nucleotides in length, optionally the at least one region is of at least 1000 nucleotides in length.

9. The method of claim 1, wherein the synthetic RNA expression vector comprising said modified primary nucleotide sequence has a reduced frequency of at least one of CpG and UpA dinucleotides compared to the synthetic RNA expression vector which comprises an unmodified primary nucleotide sequence, and exhibits increased open reading frame (ORF) expression as compared to the synthetic RNA expression vector which comprises an unmodified primary nucleotide sequence.

10. The method of claim 1, wherein the frequency of at least one of CpG and UpA dinucleotides in the at least one region of said primary nucleotide sequence which is modified is reduced by at least 50%, optionally by at least 60%, optionally by at least 70%, optionally by at least 80%, optionally by at least 90%, optionally by at least 95%, optionally by 100%, as compared to the unmodified primary nucleotide sequence.

11. The method of claim 1, wherein the frequency of CpG dinucleotides and the frequency of UpA dinucleotides in the at least one region of said primary nucleotide sequence which is modified is reduced by at least 50%, optionally by at least 60%, optionally by at least 70%, optionally by at least 80%, optionally by at least 90%, optionally by at least 95%, optionally by 100%, as compared to the unmodified primary nucleotide sequence.

12. The method of claim 1, wherein the frequency of CpG dinucleotides and/or the frequency of UpA dinucleotides in the at least one region of said primary nucleotide sequence which is modified is reduced via introduction of synonymous substitutions into coding regions of said primary nucleotide sequence, as compared to the unmodified primary nucleotide sequence.

13. The method of claim 1, wherein the frequency ratio of the at least one of CpG and UpA dinucleotides is 0.4 or lower, optionally 0.3 or lower, optionally 0.2 or lower, optionally 0.1 or lower in the synthetic RNA expression vector as a whole.

14. The method of claim 1, wherein the frequency of CpG dinucleotides and/or the frequency of UpA dinucleotides is reduced in open reading frames (ORFs) and/or coding regions of the synthetic RNA expression vector, as compared to ORFs and/or coding regions of the synthetic RNA expression vector which comprises an unmodified primary nucleotide sequence.

15. The method of claim 1, wherein regions totaling at least 50% of the synthetic RNA expression vector are modified, optionally wherein regions totaling at least 60% of the synthetic RNA expression vector are modified, optionally wherein regions totaling at least 70% of the synthetic RNA expression vector are modified.

16. The method of claim 1, wherein the at least one region of said primary nucleotide sequence which is modified to reduce the frequency of at least one of CpG and UpA dinucleotides is a viral open reading frame (ORF), optionally a viral ORF derived from a viral genome.

17. The method of claim 1, wherein the synthetic RNA expression vector comprises a RNA virus adapted for expression in an expression system for the production of a virus vaccine, optionally wherein the virus vaccine expresses heterologous pathogen antigens.

18. The method of claim 1, wherein the synthetic RNA expression vector is present in a viral replicon.

19. The method of claim 1, wherein the synthetic RNA expression vector is present in a viral replicon, optionally wherein replication of the viral replicon in a mammalian cell is enhanced relative to a viral replicon containing the synthetic RNA expression vector which comprises an unmodified primary nucleotide sequence.

20. A method of producing a synthetic recombinant ssRNA virus genome, the method comprising:
   modifying at least one region of a primary ssRNA virus genome to reduce the frequency of CpG and UpA dinucleotides in said at least one region of the primary ssRNA virus genome, thereby producing one or more modified regions of the primary ssRNA virus genome; and
   producing a synthetic recombinant ssRNA virus genome comprising said one or more modified regions which have a reduced frequency of CpG and UpA dinucleotides compared to synthetic ssRNA virus genome which comprises an unmodified primary ssRNA virus genome.

* * * * *